US005888818A

United States Patent [19]

Cronin et al.

[11] Patent Number: 5,888,818

[45] Date of Patent: Mar. 30, 1999

[54] HERBICIDE RESISTANT PLANTS

[75] Inventors: Kathryn Elizabeth Cronin, Maidenhead; John Raymond Ellis, deceased, late of Marlowe, by Roland Richard Ellis, legal representative; Patrick Joseph Hussey, Windsor; John Anthony Ray, Bracknell, all of England; Teresa Ruth Waldin, Bridgend, Wales

[73] Assignee: Zeneca Limited, London, England

[21] Appl. No.: 343,475

[22] PCT Filed: May 26, 1993

[86] PCT No.: PCT/GB93/01085

§ 371 Date: Nov. 25, 1994

§ 102(e) Date: Nov. 25, 1994

[87] PCT Pub. No.: WO93/24637

PCT Pub. Date: Dec. 9, 1993

[30] Foreign Application Priority Data

May 26, 1992 [GB] United Kingdom ................... 9211130

[51] Int. Cl.$^6$ .......................... C12N 15/00; C12N 15/09; C12N 15/05; A01H 1/06

[52] U.S. Cl. .......................... 435/418; 435/410; 435/419; 435/172.3; 435/172.1; 800/205; 536/23.1; 536/23.6; 935/10; 935/67; 935/69; 935/72; 935/76

[58] Field of Search .......................... 800/205; 536/24.1, 536/26.7, 23.1, 23.6; 435/8, DIG. 1, 257, 946, 317.1, 410, 418, 419; 938/10, 67; 935/68, 69, 72, 76

[56] References Cited

U.S. PATENT DOCUMENTS 5,484,956 1/1996 Lundquist et al. ...................... 800/205

OTHER PUBLICATIONS

Alexandraki et al. "Sequence heterogeneity, multiplicity, and genomic organization of alpha and beta tublin genes in sea urchins" Molecular and Cellular Biology, pp. 1125–1137, Dec. 1981.

Takahashi et al: "Molecular basis for determining the sensitivity of eucaryotes to the antimitotic drug rhizoxin" Mol.Gen Genet (1990) 222: 167–175.

Lee et al: "Missense Mutations at Lysine 350 in β2–Tublin Confer Altered Sensitivity to Microtubule Inhibitors in Chlamydomonas", The Plabt Cell. vol. 2, 1051–1057, Nov. 1990.

Vaughn, et al: "Structural and Biochemical Characterization of Dinitroaniline–Resistant Eleusine", ACS Symp.Ser. vol. 421, 1990, pp. 364–375.

Schibler, et al: "The colr4 and colr15 beta–tubulin mutations in Chyamydomonas reinhardtii confer altered sensitivities to microtubule inhibitors and herbicides by enhancing microtubule stability", Biological Abstracts vol. 92, 1991, abstracr No. 4602, and J Cell Biol, vol. 113, No. 3, 1991 pp. 605–614.

Silflow et al: "Herbicide–resistant mutants in Chlamydomonas with degects in an alpha tubulin gene", J. Cell Biol. vol. 107, 1988, 6 part 3, p. 670A.

Ellis, et al: "Tubulin isotype expression in two herbicide resistant and sensitive species", J.Cell Biochem, Suppl. vol. 16F, 1992, p. 231.

*Primary Examiner*—Gary Benzion
*Attorney, Agent, or Firm*—Melissa A. Shaw

[57] ABSTRACT

The invention provides a modified tubulin comprising a tubulin polypeptide which confers resistance to an anti-tubulin agent when expressed within a biological organism, said polypeptide having at least one amino acid substitution such that hydrophobicity is increased at one or more positions in the polypeptide. DNA sequences encoding such modified tubulins may be used to confer resistance on organisms which otherwise would be susceptible to one or more anti-tubulin agents. For example, a plant which is resistant to a herbicide that disrupts microtubule structure or function may be produced.

13 Claims, 8 Drawing Sheets

HERBICIDE RESISTANT PLANTS

This invention relates to modified tubulins, DNA sequences encoding such tubulins and organisms transformed with such DNA.

Almost all eukaryotic cells contain microtubules which comprise a major component of the network of proteinaceous filaments known as the cytoskeleton. Microtubules thereby participate in the control of cell shape and intracellular transport. They are also the principal constituent of mitotic and meiotic spindles, cilia and flagella. In plants, microtubules have additional specialized roles in cell division and cell expansion during development.

In terms of their composition, microtubules are proteinaceous hollow rods with a diameter of approximately 24 nm and highly variable length. They are assembled from heterodimer subunits of an α-tubulin and a β-tubulin polypeptide, each with a molecular weight of approximately 50,000. Both polypeptides are highly flexible globular proteins (approximately 445 amino acids), each with a predicted 25% α helical and 40% β-pleated sheet content. In addition to the two major forms (α-and β-tubulin), there is a rare γ-tubulin form which does not appear to participate directly in the formation of microtubule structure, but rather it may function in the initiation of microtubule structure.

In all organisms, the multiple α- and β-tubulin polypeptides are encoded by corresponding families of α- and β-tubulin genes, which are located in the nuclear genome. Many such genes (or corresponding cDNAs) have been isolated and sequenced. For example, maize has approximately 6 α-tubulin genes and approximately 8 β-tubulin genes dispersed over the genome (Villemur et al, 1992, 34th Maize Genetics Symposium). Some of the α-tubulin genes from maize have been cloned and sequenced (Montoliu et al, 1989, Plant Mol Biol, 14, 1–15; Montoliu et al, 1990, Gene, 94, 201–207; Villemur et al, 1992, J Mol Biol, 227:81–96), as have some of the β-tubulin genes (Hussey et al, 1990, Plant Mol Biol, 15, 957–972). Comparison of amino acid sequences of the three documented maize α-tubulins indicates they have 93% homology. Maize β-tubulins exhibit 38% identity with these α-tubulins. In segments of divergence between the α- and β-tubulin amino acid sequences, homology ranges from 13% to 17%. Homology between the three α-tubulin amino acid sequences within these same α-/β-divergence regions ranges from 77% to 96%.

Sequence information on the various tubulin forms shows that throughout evolution the protein domains involved in polymerization have been highly conserved, and interspecies amino acid sequence homology is generally high. For example, the four β-tubulin isotypes in human are identical with their counterparts in mouse. There is 82–90% homology between mammalian neuronal or constitutively expressed tubulins and algal, protozoan and slime mould tubulins. Considering plant sequences in more detail, there are long stretches in which the amino acid sequence of all the α- and β-tubulins are identical (Silflow et al, 1987, Developmental Genetics, 8, 435–460). For example, the 35 amino acids in positions 401–435 are identical in all plant α-tubulins, as are the 41 amino acids in the region between positions 240 and 281 in the plant β-tubulins. Conservation of amino acid residues is approximately 40% between the α- and β-tubulin families, and 85–90% within each of the α- and β-tubulin families. It should be noted that in general, most α-tubulins are 1 to 5 residues larger that the β-tubulins.

The economic interest of tubulins lies in the effect of certain agents which interfere with tubulin structure and/or function. Such agents (including non-chemical stresses) are hereinafter referred to as "anti-tubulin agents" as they share a similar type of mode of action. Extreme conditions are known to destabilize the tubulins and/or microtubules. Such conditions include cold, pressure and certain chemicals. For example, Correia (1991, Pharmac Ther, 52:127–147) describes α- and β-tubulin interactions, microtubule assembly and drugs affecting their stability. Some anti-tubulin agents are often called "spindle poisons" or "antimitotic agents" because they cause disassembly of microtubules which constitute the mitotic spindle. For at least one hundred years, it has been known that certain chemical agents arrest mammalian cells in mitosis, and of these agents the best known is colchicine which was shown in the mid-1960s to inhibit mitosis by binding to tubulin. Many of these anti-tubulin agents have since found widespread use as cancer therapeutic agents (eg vincristine, vinblastine, podophyllotoxin), estrogenic drugs, anti-fungal agents (eg griseofulvin), antihelminthics (eg the benzimidazoles) and herbicides (eg the dinitroanilines). Indeed some of the specific agents have uses against more than one class of organism. For example, the dinitroaniline herbicide trifluralin has recently been shown to inhibit the proliferation and differentiation of the parasitic protozoan Leishmania (Chan and Fong, 1990, Science, 249:924–926).

The dinitroaniline herbicides may be considered as an example of one group of anti-tubulin agents. Dinitroaniline herbicides are widely used to control weeds in arable crops, primarily for grass control in dicotyledonous crops such as cotton and soya. Such herbicides include trifluralin, oryzalin, pendimethalin, ethalfluralin and others. The herbicidally active members of the dinitroaniline family exhibit a common mode of action on susceptible plants. For example, dinitroaniline herbicides disrupt the mitotic spindle in the meristems of susceptible plants, and thereby prevent shoot and root elongation (Vaughn KC and Lehnen LP, 1991, Weed Sci, 39:450–457). The molecular target for dinitroaniline herbicides is believed to be tubulin proteins which are the principle constituents of microtubules (Strachan and Hess, 1983, Pestic Biochem Physiology, 20, 141–150; Morejohn et al, 1987, Planta, 172, 252–264).

The extensive interest in anti-tubulin agents in many branches of science has been accompanied by the identification of several mutants shown to resist the action of such agents (Oakley BR, 1985, Can J BIochem Cell Biol, 63:479–488). Several of these mutants have been shown to contain modified α- or β- tubulin genes, but to date the only resistant mutants to be fully characterised and sequenced are those in β-tubulin. For example, colchicine resistance in mammalian cell lines is closely associated with modified β-tubulin polypeptides (Cabral et al, 1980, Cell, 20, 29–36); resistance to benzimidazole fungicides has been attributed to a modified β-tubulin gene, for example in yeast (Thomas et al, 1985, Genetics, 112, 715–734) and Aspergillus (Jung et al, 1992, Cell Motility and the Cytoskeleton, 22:170–174); some benzimidazole resistant forms of nematode are known; and dinitroaniline-resistant Chlamydomonas mutants possess a modified β-tubulin gene (Lee and Huang, 1990, *Plant Cell,* 2, 1051–1057). Some of these mutants, although resistant to one anti-tubulin agent, also show increased susceptibility to other anti-tubulin agents (such as cold stress).

Among certain weed species, some biotypes have evolved resistance to dinitroaniline herbicides. Three examples of species in which dinitroaniline resistant (R) biotypes have emerged are goosegrass, *Eleusine indica* (Mudge et al, 1984, Weed Sci, 32, 591–594); green foxtail, *Setaria viridis* (Morrison et al, 1989, Weed Technol, 3, 554–551); and *Amaranthus palmeri* (Gossett et al, 1992, Weed Technology, 6:587–591). These resistant (R) biotypes emerged following selective pressure exerted by repeated application of trifluralin. A range of resistant biotypes of each species exists but the nature and source of the resistance trait is unclear and the biotypes are genetically undefined. The R biotypes of these species exhibit cross-resistance to a wide range of dinitroaniline herbicides, including oryzalin, pendimethalin and ethalfluralin. All dinitroaniline herbicides have a similar mode of action and are therefore believed to share a common target site. Many of the R biotypes are also cross-resistant to other herbicide groups such as the phosphorothioamidates, which include amiprophos-methyl and butamifos, or chlorthal-dimethyl. The phenomenon of cross-resistance exhibited by resistant biotypes strongly indicates that the herbicide resistance trait is a consequence of a modified target site. In addition, the resistant biotypes appear to have no competitive disadvantage as they grow vigorously and can withstand various stresses (such as cold).

It has not been previously shown which specific gene is modified in *Eleusine indica* or *Setaria viridis* to confer the dinitroaniline resistance trait. Research by K. C. Vaughn and M. A. Vaughn (American Chemical Society Symposium Series, 1989, 364–375) showed an apparent alteration in the electrophoretic properties of β-tubulin present in an R biotype of *Eleusine indica*, and suggested dinitroaniline resistance results from the presence of a modified β-tubulin polypeptide. The results of recent work by Waldin, Ellis and Hussey (1992, Planta, 188:258–264) provide no evidence that dinitroaniline herbicide resistance is associated with an electrophoretically modified β-tubulin polypeptide in the resistant biotypes of *Eleusine indica*or *Setaria viridis* which were studied.

Recombinant DNA technology allows genes to be transferred between sexually incompatible organisms. Using these techniques, resistance genes can be introduced into organisms from unrelated species. For example, herbicide resistant crop plants may be produced. The purpose in providing crop plants which resist the action of a herbicide is to facilitate the destruction of weeds growing between the plants by the overall application of an effective concentration of a herbicide which would destroy the crop plant in its normal, that is herbicide sensitive, state. Such resistant plants are also useful for use in a locus of any short term carry-over of herbicide from a previous application.

An object of the present invention is to provide genetic material for use in imparting resistance to anti-tubulin agents to a biological organism. In this context, a resistant organism is defined as one which displays enhanced tolerance to an anti-tubulin agent when compared to a standard organism. Resistance may vary from a slight increase in tolerance to the effects of the anti-tubulin agent to total resistance where the organism is unaffected by the presence of agent at several times the normal level.

For example, pre-emergent or pre-plant use of dinitroaniline herbicides is precluded when maize (*Zea mays*) is grown because the seedlings and young plants of this crop are injured by these herbicides. The availability of maize hybrids which are resistant to dinitroaniline herbicides would allow the beneficial control of weeds in this crop by application of such herbicides.

According to a first aspect of the present invention, there is provided a modified tubulin comprising a tubulin polypeptide which confers resistance to an anti-tubulin agent when expressed within a biological organism, said polypeptide having at least one amino acid substitution such that hydrophobicity is increased at one or more positions in the polypeptide.

Such modified tubulins may be used to confer resistance on organisms which otherwise would be susceptible to one or more anti-tubulin agents. In addition, the modified tubulins may be used to develop diagnostic kits to detect resistance in human or other cell lines (eg using specific antibodies derived from the tubulins). Such kits may be used for medical purposes (eg to detect drug resistance in nematode parasites) or for agricultural purposes (eg enabling fast identification of herbicide resistant plants which are tubulin mutants). The modified tubulin protein may also be useful in separation columns or in screening methods relying on the binding of anti-tubulin agents.

Modified tubulins according to the invention may be isolated from a biological organism which is naturally resistant to one or more anti-tubulin agents. Such organisms include yeast, fungi, algae, animals and plants (for example, weed biotypes of *Eleusine indica, Setaria viridis*, or *Amaranthus palmeri* which have evolved resistance to dinitroaniline herbicides).

We have isolated and characterised a modified tubulin obtainable from the dinitroaniline resistant ($R^+$) biotype of *Eleusine indica* (goosegrass), deposited as seed at The National Collections of Industrial and Marine Bacteria (23 St Machar Drive, Aberdeen, Scotland, AB2 1RY) under the terms of the Budapest Treaty on 11 May 1992 under the accession number NCIMB 40504. This modified tubulin belongs to the α-tubulin family and, being the most abundant tubulin, is designated as the α1-tubulin isotype. This specific α1-tubulin is a modified polypeptide which is present only in the $R^+$ biotype and confers dinitroaniline resistance. The distinctive electrophoretic properties of this α1-tubulin differentiate it from the α1 isotype found in the susceptible (S) biotype (see Example 2). The modified α1-tubulin isolated from seedlings of the resistant ($R^+$) biotype of goosegrass is "shifted" towards an apparently higher molecular weight (slower migration in 2D gels) and more acidity (lower pI) compared to the equivalent α1-tubulin isolated from seedlings of the susceptible (S) biotype.

According to a second aspect of the invention, there is provided a DNA construct comprising a DNA sequence encoding a modified tubulin polypeptide which confers resistance to an anti-tubulin agent when expressed within a biological organism, said polypeptide having at least one amino acid substitution such that hydrophobicity is increased at one or more positions in the polypeptide.

Such DNA constructs may be used to confer resistance on organisms which otherwise would be susceptible to one or more anti-tubulin agents. For example, the modified tubulin sequence may be used as a selectable marker in transformation experiments involving any cell type (including bacterial, fungal, plant or animal cells). Standard techniques are employed (as described for β-tubulin mutations used as selectable markers in Aspergillus, Cercospora and Septoria: Cooley et al, J Gen Microbiol, 1991, 137:2085–2091; Upchurch et al, 1991, Appl Env Microbiol, 57(10):2935–2939; Seip et al, 1990, App Env Microbiol, 56(12):3686–3692). In addition, the constructs may be used to develop diagnostic DNA probes (which may be sensitive enough to detect a single base change) for medical, agricultural or other purposes.

The DNA sequence encoding the modified tubulin may be synthesised ab initio or may be isolated from a biological organism which is naturally resistant to one or more anti-tubulin agents. Such organisms include yeast, fungi, algae, animals and plants (for example, seeds or plants or cell cultures of a herbicide resistant biotype).

In the *Eleusine indica* $R^+$biotype, the DNA encoding the modified α1-tubulin (a modified polypeptide component of the target site for dinitroaniline herbicides) is the "herbicide resistance gene" responsible for the resistance trait. A cDNA clone (hereinafter called $R^+$#2) encoding the modified α1-tubulin has been isolated and sequenced. The coding sequence differs from that of the equivalent cDNA clone (S#15) isolated from the susceptible (S) biotype to give a particular amino acid substitution (isoleucine for threonine) at position 239. This is the first α-tubulin mutant to have been sequenced.

The single base change C to T in $R^+$#2 is the most significant sequence difference between the α1-tubulin genes from the susceptible (S) and resistant ($R^+$) plants. It results in the amino acid substitution $Thr^{239}$ (threonine predicted by the codon ACA in the S biotype) to $Ile^{239}$ (isoleucine predicted by the codon ATA in the $R^+$biotype). A degree of nucleotide variation between the biotypes which is unrelated to the dinitroaniline resistance trait may be due to genetic polymorphism. However, the significance of the sequence modification is emphasised by the unusual codon used at the $Ile^{239}$ position. The C to T mutation results in the codon ATA for isoleucine in $R^+$#2. The ATA codon is not used to code for isoleucine in the wild type molecule (S#15 from the susceptible biotype) and hence is not a preferred codon. (The isoleucines at all other positions in the modified α1-tubulin from the $R^+$ biotype and in the unmodified α1-tubulin from the S biotype are predicted by other codons, as shown in Table 1).

TABLE 1

CODON USAGE IN THE E INDICA α1-TUBULIN CLONES

| | | | | |
|---|---|---|---|---|
| | Unmodified α1-tubulin cDNA clone (S#15) (Susceptible biotype) | | | |
| THR: | act | acc | aCa | acg |
| | 4 | 17 | 1 | 1 |
| ILE: | att | atc | ata | |
| | 5 | 18 | 0 | |
| | Modified α1-tubulin cDNA clone ($R^+$#2) (Resistant biotype) | | | |
| THR: | act | acc | aca | acg |
| | 4 | 17 | 0 | 1 |
| ILE: | att | atc | aTa | |
| | 5 | 18 | 1 | |

In addition, there is remarkable conservation of amino acid sequence of tubulin polypeptides throughout the diversity of eukaryotic phylogenic groups. This suggests that selection pressure has acted against mutations in tubulin genes which cause amino acid substitutions that may disrupt tubulin function. In general, the sequences of tubulins from different organisms are relatively similar both within and between the different tubulin forms (α, β and γ): amino acid sequences of certain segments or single amino acids at certain positions of the polypeptide appear to be invariant (see FIG. 5 in Silflow et al, 1987, Developmental Genetics, 8, 435–460). For example, $Thr^{239}$ is conserved in the five sequenced α-tubulin genes/cDNAs of maize (tua1, 2, 3, 5 and 6) and in the six sequenced α-tubulins of Arabidopsis. Indeed, threonine is found at an equivalent position in each of the 99 tubulin protein sequences (α-, β- and γ-tubulins) which have been examined, as described below.

The Swiss-Prot Version 23 database contains sequences covering all forms of life (including mammals, plants, insects, fungi and bacteria). A search for tubulin proteins using the IG-Suite program FINDSEQ retrieved 113 protein sequences. Of these, 41 α-tubulin, 53 β-tubulin and 5 γ-tubulin full length sequences were aligned using the IG-Suite program GENALIGN resulting in the α-, β- and γ-tubulin consensus sequences for the region shown in Table 2. The indicated amino acid positions (*) relating β- and γ-tubulins to α-tubulin $Threonine^{239}$ are based on the "average" position of the conserved threonine within each class of tubulin. The $Thr^{239}$-equivalent position (*) falls within a sequence designated as "compact domain 2" (residues 165–260) of tubulin polypeptides by Fosket and Morejohn (1992, Ann Rev Pl Phys, 43:201–240). Table 2 shows the overall consensus within the region. It also shows those amino acids with 100% identity in all the individual tubulin sequences used for the comparison (including the $Thr^{239}$-equivalent residues marked by *).

TABLE 2

ALIGNMENT OF α-, β- AND γ-TUBULIN CONSENSUS SEQUENCES

| | |
|---|---|
| | *239 |
| α-tubulin - | RPTYTNLNRLIAQVVSSITASLRFDGALNVDLTEFQT |
| | *237 |
| β-tubulin - | TPTYGDLNHLVSATMSGVTTCLRFPGQLNADLRKLAV |
| | *240 |
| γ-tubulin - | NPSFSQINQLVSTIMSASTTTLRYPGYMNNDLIGIIA |
| | * |
| consensus - | -PTY--LN-LVS--MS--TT-LRFPG-LN-DL------ |
| identity - | -P-------L---------T---R-----N------------ |

In summary, the wild type α1-tubulin from the *E indica* susceptible biotype contains the $Thr^{239}$ residue which is typical of known tubulin proteins. However, the modified α1-tubulin from the resistant ($R^+$) biotype contains a unique amino acid substitution: the $Ile^{239}$ residue which is encoded by a unique codon within the protein. This suggests that the substitution of isoleucine in a tubulin at a position equivalent to the asterisk in Table 2 (usually 239 in a α-tubulin, 237 in a β-tubulin and 240 in a γ-tubulin) of any biological organism may produce a modified tubulin which confers resistance to an anti-tubulin agent when expressed within the organism. In fact, the substitution of any one or more amino acids which results in an equivalent alteration in physical properties of the polypeptide may produce a modified tubulin which confers such resistance.

The modified α1-tubulin has altered physical properties which are detectable as an altered hydropathy profile. The hydropathy of proteins is known to differ between organisms; for example, Silflow et al (1987, Dev Genetics, 8:435–460) have compared the hydropathy profile of animal and plant tubulins. Using the IG-Suite program SOAP, the hydropathic index of a selected protein can be evaluated along its sequence according to the method of Kyte and Doolittle (1982, J Mol Biol, 157:105–132). FIG. 1 shows the hydropathy profile of sequence ELS15 (the protein sequence of the unmodified (α1-tubulin from the susceptible *E indica* biotype); FIG. 2 shows the hydropathy profile of sequence ELR2 (the protein sequence of the modified α1-tubulin from the resistant $R^+$biotype). Both the ELS15 and the ELR2 sequences have a total of 451 amino acids. The hydropathic index of both sequences was computed using an interval of nine amino acids from amino acid 180 to amino acid 270. A comparison of FIGS. 1 and 2 reveals a significant change in the region covering amino acid positions 237–240 which increases in relative hydrophobicity from approximately 15 in the unmodified protein to over 20 in the modified protein. This shift in hydrophobicity is distinctive of the ELR2-type of modified tubulin: it is apparently not found in other modified tubulins known to be associated with resistance to anti-tubulin agents. For example, the hydropathic index of a yeast β-tubulin was evaluated using the method of Kyte and Doolittle as described above. The β-tubulin (total 457 amino acids) also occurs in a mutated form which confers resistance to colchicine in yeast and has an arginine to histidine substitution at position 241 (Thomas et al, 1985, Genetics, 112:715–734). FIG. 3 shows the hydropathy profile of the wild-type β-tubulin, and FIG. 4 shows the hydropathy profile of the mutant β-tubulin. The hydropathic index of both sequences was computed using an interval of nine amino acids from amino acid 180 to amino acid 270. Comparison of FIGS. 3 and 4 does not reveal any significant difference in the hydropathy profile: there is no increase in hydrophobicity at the mutation site.

The distinctive shift in the hydropathy profile of the modified tubulin according to the invention affects the three-dimensional structure of the polypeptide. This change in conformation presumably alters the affinity and/or binding site(s) for anti-tubulin agents directly (by altering the α1-tubulin/agent interaction) or indirectly (by altering the α-/β-tubulin interaction or by altering the binding of microtubule associated protein), and results in the modified tubulin conferring resistance to such agents.

In the modified (α1-tubulin from the resistant $R^+$*E indica* biotype, the substitution of $Thr^{239}$ with Ile $^{239}$ replaces a polar (hydrophilic) residue ($—C_2H_4OH$) with a non-polar (hydrophobic) residue ($C_4H_9$). None of the known β-tubulin mutants show this distinctive polar to non-polar amino acid change.

In a DNA construct according the invention, the DNA sequence encoding the modified tubulin preferably encodes an altered amino acid at a position equivalent to 239 of an α-tubulin, 237 of a β-tubulin, 240 of a γ-tubulin. Preferably the altered amino acid is isoleucine, but substitution with other amino acids which give the required effect on polypeptide structure/function is also possible (for example nonpolar amino acids such as leucine or valine).

For example, the DNA sequence encoding the modified tubulin may be a cDNA or genomic DNA or synthetic DNA sequence corresponding to the sequence of the cDNA clone $R^+$#2 which is given in Table 3 below. The related genomic DNA may be isolated by screening a genomic library with suitable probes derived from the cDNA sequence. Clone $R^+$#2 has been deposited at The National Collections of Industrial and Marine Bacteria (23 St Machar Drive, Aberdeen, Scotland, AB2 1RY) under the terms of the Budapest Treaty on 24 May 1993 under the accession number NCIMB 40558.

TABLE 3

DNA SEQUENCE OF CLONE $R^+$ #2

| | 10 \| 20 \| 30 \| 40 \| 50 \| |
|---|---|
| 1 | CTCGCCTCTCTCCGCGACTCCAAGCTTTCTCCCTCCTCCCATTTCCCGTC |
| 51 | GCCGCCGCCTCACCCGCCCGACACCATGAGGGAGTGCATCTCGATCCACA |
| 101 | TCGGCCAGGCCGGTATCCAGGTCGGAAACGCTTGCTGGGAGCTCTACTGC |
| 151 | CTCGAGCATGGCATCCAGGCTGACGGTCAGATGCCCGGTGACAAGACCAT |
| 201 | TGGAGGAGGTGATGATGCTTTCAACACCTTCTTCAGTGAGACTGGCGCCG |
| 251 | GCAAGCATGTGCCCCGTGCCGTGTTTGTTGACCTTGAGCCCACTGTGATC |
| 301 | GATGAGGTCAGGACTGGCACCTACCGCCAGCTGTTTCACCCTGAGCAGCT |
| 351 | CATCAGTGGCAAGGAGGATGCTGCCAACAACTTTGCCCGTGGTCACTACA |
| 401 | CCATTGGCAAGGAGATTGTTGACCTGTGCCTTGACCGCATCAGGAAGCTT |
| 451 | GCCGACAACTGTACTGGTCTCCAGGGCTTCCTTGTCTTCAACGCTGTCGG |
| 501 | TGGAGGAACGGGCTCTGGTCTTGGTTCCCTCCTCCTTGAGCGCCTGTCTG |

TABLE 3-continued

| DNA SEQUENCE OF CLONE R⁺ #2 | |
|---|---|
| 551 | TTGACTACGGCAAGAAGTCCAAGCTCGGGTTCACTGTCTACCCGTCTCCC |
| 601 | CAGGTCTCCACCTCGGTGGTTGAGCCATACAACAGTGTGCTGTCCACCCA |
| 651 | CTCCCTCCTTGAGCACACCGATGTGGCTGTGCTGCTTGACAACGAGGCCA |
| 701 | TCTACGACATCTGCCGCCGCTCCCTGGACATTGAGCGCCCAACCTACACC |
| 751 | AACCTGAACAGGCTTGTTTCTCAGGTCATTTCATCACTGATAGCCTCTCT |
| 801 | GAGGTTCGATGGTGCTCTGAACGTGGATGTGAACGAGTTCCAGACCAACT |
| 851 | TGGTGCCCTACCCGAGGATCCACTTCATGCTTTCATCCTACGCTCCAGTG |
| 901 | ATCTCCGCGGAGAAGGCCTACCACGAGCAGCTGTCCGTGGCTGAGATCAC |
| 951 | CAACAGCGCGTTCGAGCCTTCCTCCATGATGGCCAAGTGCGACCCCCGCC |
| 1001 | ACGGCAAGTACATGGCCTGCTGCCTCATGTACCGTGGTGATGTGGTGTCC |
| 1051 | AAGGACGTGAACGCCGCCGTTGCCACCATCAAGACCAAGCGCACCATCCA |
| 1101 | GTTCGTGGACTGGTGCCCCACTGGCTTCAAGTGCGGTATCAACTACCAGC |
| 1151 | CACCCAGCGTCGTCCCCGGCGGCGACCTGGCCAAGGTGCAGAGGGCCGTG |
| 1201 | TGCATGATCTCCAACTCCACCAGTGTCGTCGAGGTGTTCTCCCGCATCGA |
| 1251 | CCACAAGTTCGACCTCATGTACGCCAAGCGCGCCTTCGTCCACTGGTACG |
| 1301 | TGGGTGAGGGTATGGAGGAGGGTGAGTTCTCCGAGGCGCGTGAGGACCTT |
| 1351 | GCTGCCCTTGAGAAGGACTACGAGGAGGTCGGCGCTGAGTTCGACGAGGG |
| 1401 | TGAGGAAGGTGATGAGGGTGACGAGTACTAGATGAATCTACGCTTCCTGC |
| 1451 | TGTTGTGTCAGGCCTGTGTGCCGCTGCTATCCTGTGATCTGCCCGAGGGC |
| 1501 | GCTATCGTGTCGTGTCAGTTTGAACTATTTGTCATTGTGTGGTTACAACC |
| 1551 | CCTGAAGTTGTAGACATGTTTAATTCAAAAAAAAAAAAAAAAA |

In a DNA construct according to the invention, the DNA sequence is generally preceded by a transcriptional initiation region operative in a biological cell so that the construct can generate mRNA in the cell. The transcriptional initiation region may be any suitable promoter which is operative in the particular cell type. Either a constitutive promoter or an inducible or developmentally regulated promoter may be used as circumstances require. Suitable plant-operative promoters include the constitutive 35S cauliflower mosaic virus promoter, the CAB promoter driving expression in green tissues, or the tomato polygalacturonase gene promoter sequence (Bird et al, 1988, Plant Molecular Biology, 11:651–662).

According to a third aspect of the invention, there is provided a method to produce a biological organism resistant to an anti-tubulin agent by transformation of a cell of the organism with a DNA construct comprising a DNA sequence encoding a modified tubulin which confers resistance to an anti-tubulin agent when expressed within a biological organism. The invention further provides a transgenic cell containing said DNA construct, and organisms derived therefrom.

For example, the modified tubulin may be used purely as a selectable marker in transformation experiments and an appropriate anti-tubulin agent is then used to select for the transgenic cells. Transgenic cells expressing the modified tubulin may also be used in mode of action and cross-resistance studies to aid the development of new drugs with an anti-tubulin mode of action.

As another example, a herbicide resistant plant may be derived from a transgenic plant cell produced by transformation of the cell with a DNA construct including the R⁺#2 DNA sequence encoding a modified α-tubulin. Expression of the modified tubulin within the plant confers increased herbicide resistance (including increased herbicide tolerance) to a herbicide with a mode of action involving disruption of microtubule structure or function.

The herbicide resistance gene (encoding the modified α-tubulin) may be transferred into any monocotyledonous or dicotyledonous plant species using standard transformation techniques (cells or callus may be subsequently regenerated into whole plants). Preferably the recipient is maize or sugarbeet, and preferably the DNA construct is stably integrated within the plant genome. These plants may be intercrossed or crossed with other plant lines to produce seeds and progeny. The transgenic plants and their progeny may be resistant to members of the dinitroaniline family of herbicides such as trifluralin, oryzalin, pendimethalin, ethalfluralin and others. The plants may also be resistant to other herbicides with a similar mode of action, such as the phosphorothioamidates or chlorthal-dimethyl.

One option is to transfer the complete gene, including flanking sequences necessary for regulated gene expression, derived from *E indica* R⁺ biotype into the recipient plant cell. Alternatively, the coding region of the gene or of the cDNA derived from *E indica* R⁺biotype, flanked by DNA regulatory sequences from another source, may be transferred into the recipient cell.

The transgenic plants and their progeny may be tested for herbicide resistance by germination and growth in the presence of a discriminatory dose of dinitroaniline, phosphorothioamidate or chlorthal-dimethyl herbicide. It is possible to evaluate the $R^+$#2 "resistance gene" in the transgenic cell culture lines as dinitroaniline resistance can be expressed in undifferentiated culture tissue. (Expression of dinitroaniline resistance in undifferentiated culture tissue was demonstrated using amorphous callus of *Setaria viridis*: tissue from the R biotype proved 10-fold more tolerant to trifluralin than tissue from the S biotype).

BRIEF DESCRIPTION OF THE DRAWINGS

The invention will now be described by way of example only with reference to the accompanying drawings in which.

EXAMPLE 1

Characterisation of a Resistant ($R^+$) Biotype of *Eleusine Indica*: Response to Dinitroaniline Herbicide To evaluate the response of susceptible (S) and resistant (R) biotypes of *Eleusine indica* (goosegrass) to dinitroaniline herbicides, seedling growth was monitored following seed germination in darkness on gelled medium supplemented with herbicide.

Seeds of a susceptible (S) and a resistant (R) biotype of *E indica* were surface sterilised in 20% (v/v) Domestos for 15 minutes, washed in sterile water and plated onto germination medium (MS salts, 20 g/l sucrose, 4 g/l Gelrite, pH 5.8). Trifluralin herbicide (2,6-dinitro-N,N-dipropyl-4-(trifluoromethyl)benzenamine) was dissolved in dimethylsulphoxide and added to cooled autoclaved medium. Plated seeds were incubated in darkness at 25° C. and length of shoot (encompassing mesocotyl, coleoptile and leaf) was measured after 5 or 6 days.

Trifluralin caused severe stunting of the shoots and roots of S biotype seedlings at concentrations which had no effect on seedlings of the R biotype.

Figure 1:
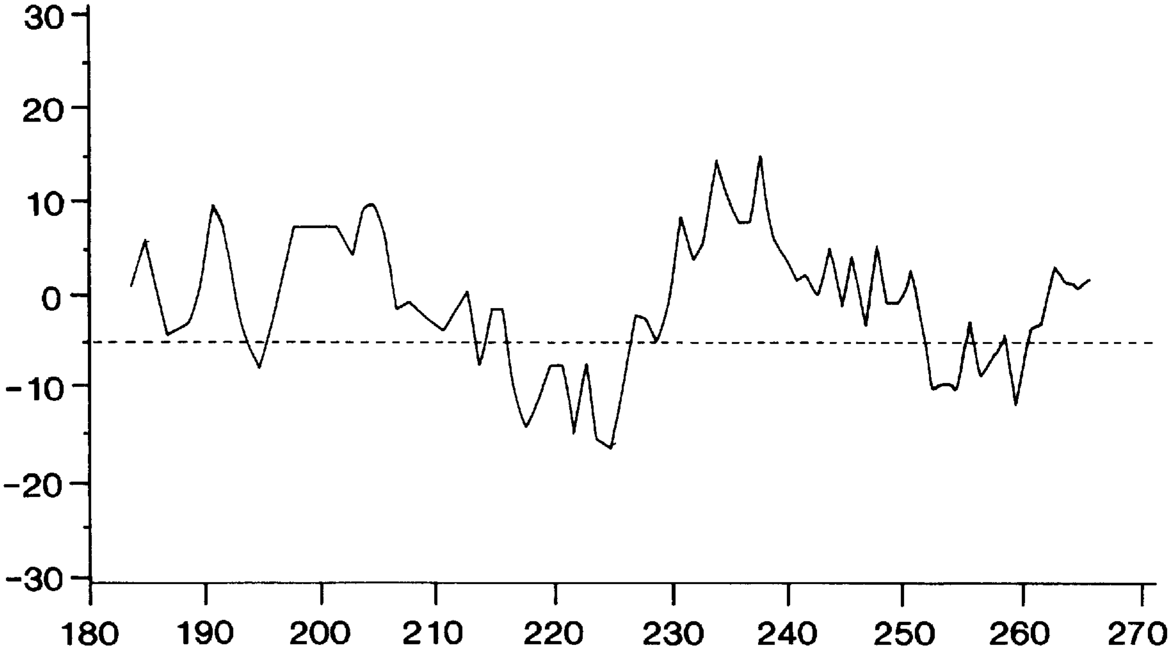
FIG. 1 is a plot of hydropathy profile for sequence ELS15.
Figure 2:
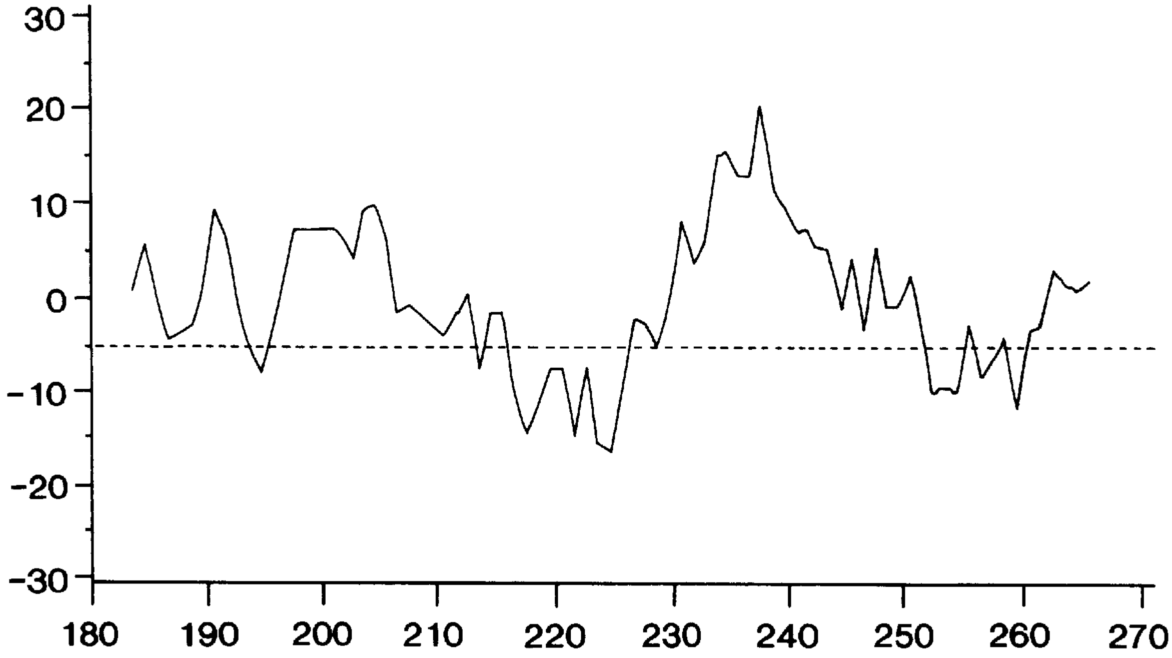
FIG. 2 is a plot of hydropathy profile for sequence ELR2.
Figure 3:
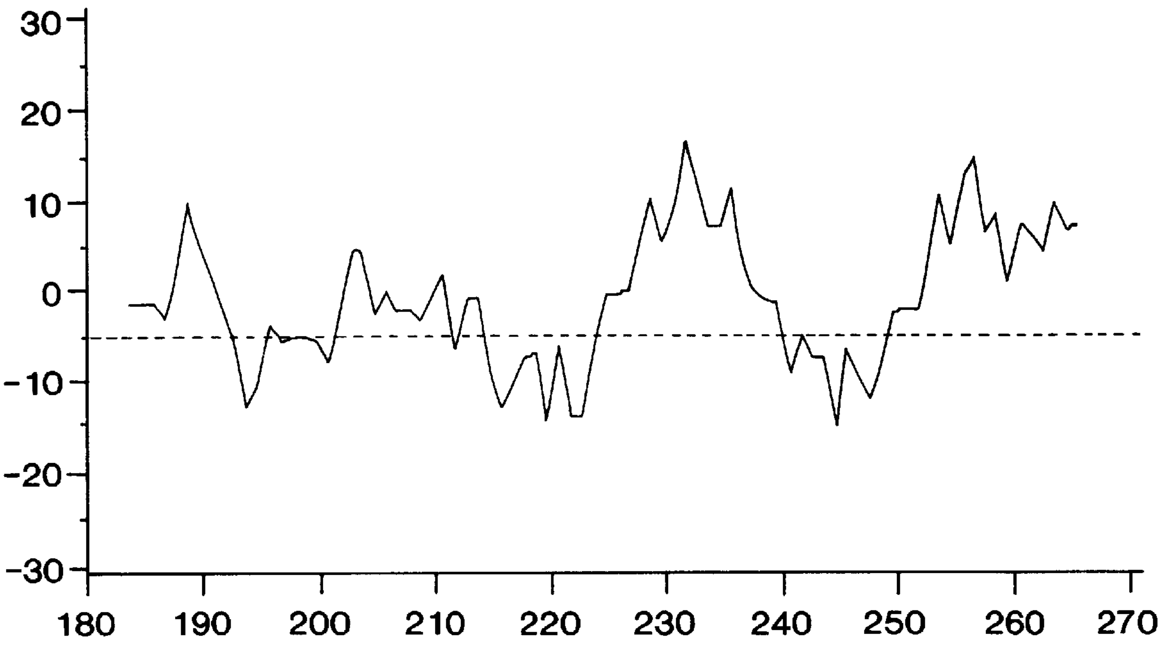
FIG. 3 is a plot of hydropathy profile for a yeast wild-type β-tubulin.
Figure 4:
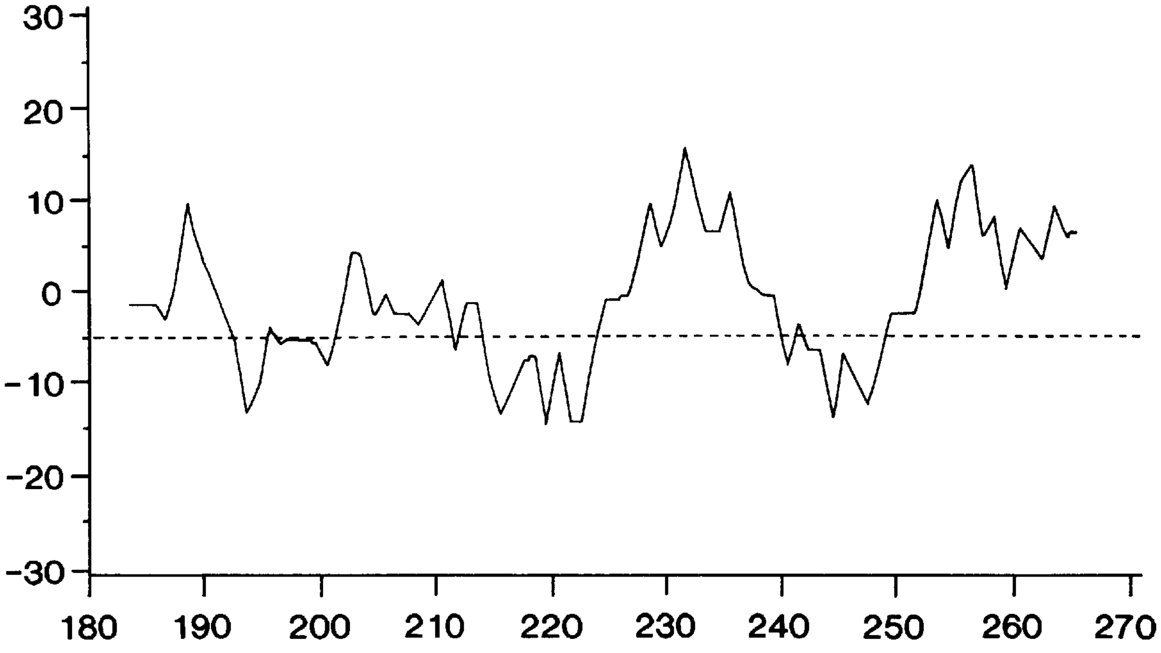
FIG. 4 is a plot of hydropathy profile for a yeast mutant β-tubulin.
Figure 5:
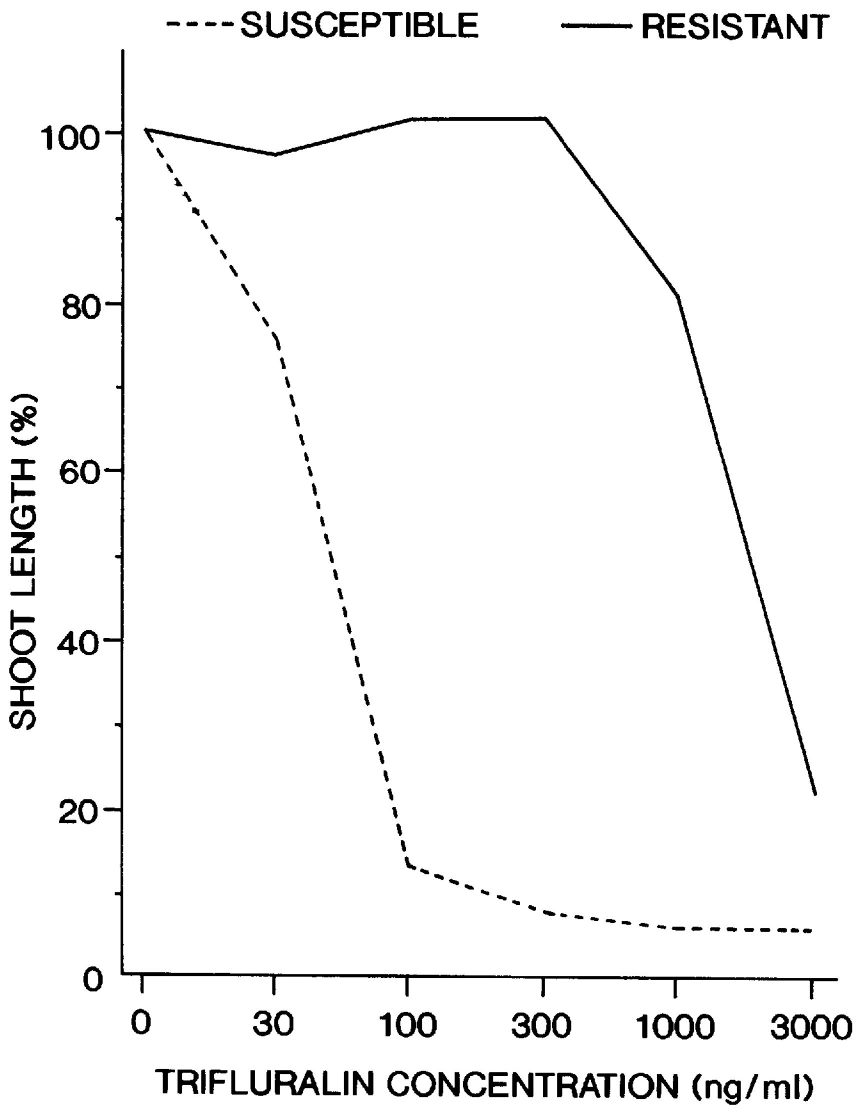
FIG. 5 shows the dose-response curves for trifluralin treatment of *Eleusine indica* seedlings.

The dose-response curves are shown in FIG. 5. Both the S and R biotypes exhibited a dose-dependent inhibition of shoot elongation on trifluralin. However, an approximately 40-fold higher concentration of trifluralin was required for equivalent injury of the R biotype relative to the S biotype, as judged by $ID_{50}$ values. ($ID_{50}$ is the concentration required for 50% growth inhibition).

Seeds of this "40-fold" resistant *E indica* biotype, designated ICITRI40 ($R^+$), were deposited at The National Collections of Industrial and Marine Bacteria on 11 May 1992 under the accession number NCIMB 40504. Cross-resistance has been demonstrated to dinitroanilines (pendimethalin, oryzalin), phosphorothioamidates (butamifos, amiprophos-methyl) and a terepthalate (chlorthal-dimethyl). No difference in sensitivity to propyzamide was found between the S and $R^+$ biotypes.

Taxol is a mitotic inhibitor which has a unique mode of action: it promotes tubulin polymerisation such that the microtubules are hyper-stabilized. The response of goosegrass to taxol was examined. Taxol proved highly potent on shoots and roots of germinating seedlings (more inhibitory than trifluralin on a molar basis). There was no evidence for differential sensitivity between the S and $R^+$ biotypes. Thus dinitroaniline resistance in goosegrass shows different characteristics from the colchicine/dinitroaniline resistance in Chlamydomonas documented by Lee and Huang (1990, Plant Cell, 2, 1051–1057). The two Chlamydomonas mutants, characterised by a point mutation in β1-tubulin (encoding a single amino acid substitution of the native $lysine^{350}$ (basic residue) to either glutamic acid (acidic residue) or methionine (non-polar residue)), exhibited cross-resistance to pronamide and super-sensitivity to taxol. Thus the molecular basis for dinitroaniline resistance in goosegrass appears to be different from that in Chlamydomonas.

EXAMPLE 2

Identification of a Modified α-Tubulin Isotype in the Resistant ($R^+$) Biotype of *Eleusine Indica*

The electrophoretic properties of α- and β-tubulin polypeptides extracted from seedlings of dinitroaniline susceptible and resistant biotypes of *Eleusine indica* were examined to determine which tubulin polypeptide has a modified amino acid composition. In both the S and $R^+$ biotypes, four α-tubulin isotypes were identified. The ICITRI40 $R^+$ resistant biotype (NCIMB 40504) differed from the S biotype by one α-tubulin isotype which exhibited lower electrophoretic mobility and lower isoelectric point (pI) than its counterpart in the susceptible biotype. This "shifted" isotype is the most abundant α-tubulin in dark-grown seedlings, as judged by the size of the immuno-stain, and is therefore designated as α1-tubulin. The experiments are described below.

The total protein from dark-grown seedlings was extracted as follows. Seedlings grown for 14 days were washed in double distilled water and crushed in liquid nitrogen. The resulting powder was solubilized by boiling in 6 ml of Laemmli sample buffer which contained 62.5 mM Tris-HCl, 10% (w/v) glycerol, 2.3% (w/v) SDS (Fisons, UK) and 5% (w/v) β-mercaptoethanol. Any insoluble material was removed by centrifugation and the proteins in the supernatant precipitated with 9 volumes of acetone at −20° C. for 3 hours. The precipitate was dried and resuspended in 100 μl of 20 mM Tris-HCl (pH 7.6), 5 mM $MgCl_2$, 1% (w/v) Nonidet P40 and 5 mg/ml leupeptin. To this thick slurry was added 4 μl of 1 mg/ml DNase and the mixture incubated on ice for 15 minutes. To a 50 μl aliquot of the mixture were added 60 mg of urea and 100 μl of 9.5M urea, 2% (w/v) Nonidet P40, 5% (w/v) β-mercaptoethanol and 2% (w/v) ampholines (3:2 ratio of pH ranges 3.5–10 and 5–7). These samples were stored at −80° C. prior to electrophoresis.

The denatured polypeptides were separated on 2-D gels, using isoelectric focusing on the first dimension and SDS-polyacrylamide gel electrophoresis on the second dimension. Two-dimensional SDS-polyacrylamide gel electrophoresis (PAGE) was executed as described by O'Farrell (1975, J Biol Chem, 250:4007–4021). The volume of protein sample loaded onto the gels ranged from 1–15 μl.

The polypeptides were blotted onto a nitrocellulose membrane, and α-tubulin or β-tubulin polypeptides were detected using specific monoclonal antibodies. Proteins were transferred from the polyacrylamide gels to nitrocellulose by the method of Towbin et al (1979, Proc Natl Acad Sci USA, 76, 4350–4354). Well-characterised IgG-type monoclonal antibodies specific to α-tubulin or β-tubulin were used to probe western blots. Bound anti-tubulin antibodies were visualised by immunoperoxidase staining (Birkett et al, 1985, FEBS Lett, 187:211–218). To detect α-tubulin TAT-1, an anti-α-tubulin antibody raised against the cytoskeleton of *Trypanosoma brucei* (Woods et al, 1989, J Cell Sci, 93, 491–500) and Amersham anti-α-tubulin antibody were used sequentially, the immunoblot being stained between and after reaction with the two antibody probes. β-tubulin was detected by probing the western blots sequentially with the antibody KMX-1 (Birkett et al, 1985) and Amersham anti-β-tubulin antibody, and with staining of the immunoblot between and after reaction with the two different antibody probes. A tubulin isotype is defined as an immunoreacting spot on a 2-D gel which is reproducibly electrophoretically separable.

Figure 6:
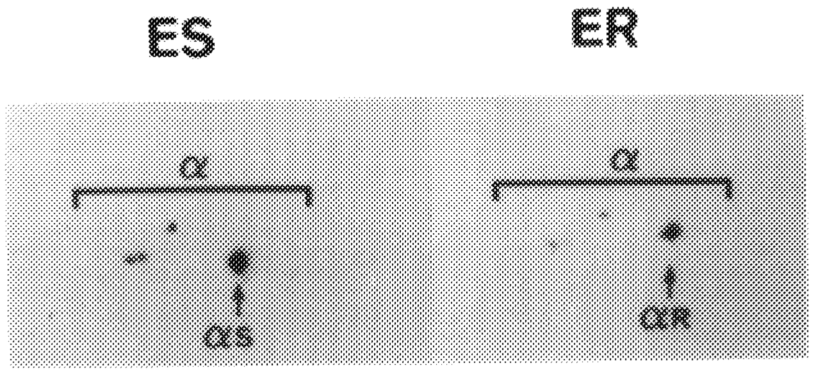
FIG. 6 shows the western blot for the α-tubulin polypeptides extracted from *Eleusine indica* seedlings.

In protein extracts from both S biotype and $R^+$ biotype seedlings, four α-tubulin isotypes and four β-tubulin isotypes were detected. FIG. 6 shows the western blot for α-tubulins from the $R^+$ resistant (ER) and susceptible (ES) biotype. The relative positions of the tubulin isotypes were closely similar in the S and $R^+$ biotypes, except for that of the most abundant α-tubulin isotype (the α1-tubulin isotype). The α1-tubulin from the $R^+$ biotype was shifted towards lower electrophoretic mobility (higher molecular weight) and lower isoelectric point (more acidic) relative to that of the S biotype.

To subject the electrophoretic data to statistical analysis, the position of the α1-tubulin isotype was measured in three pair-wise comparisons (S and $R^+$ processed in parallel on each of three dates). The position was scored as the angle between a line drawn from α1 to α2 isotypes and a line drawn from α2 to α3/α4 isotypes. Each measurement was replicated three or four times. Analysis of variance confirmed that the position of the α1-tubulin isotype was statistically different between the S and $R^+$ biotypes ($p<0.0001$).

TABLE 4

ANGLE DEFINING THE POSITION OF THE α1-TUBULIN ISOTYPE RELATIVE TO THE α2, α3 AND α4 ISOTYPES

| biotype | S | $R^+$ | S | $R^+$ | S | $R^+$ |
|---|---|---|---|---|---|---|
| x | 110.8 | 131.0 | 127.5 | 133.1 | 73.8 | 120.7 |
| n | 5 | 5 | 4 | 4 | 5 | 5 |
| SD | 1.92 | 6.19 | 2.04 | 1.89 | 2.28 | 2.02 |
| SE | 0.86 | 2.77 | 1.02 | 0.94 | 1.02 | 0.90 |

(x = angle in degrees)

EXAMPLE 3

Identification of the Gene Conferring Dinitroaniline Resistance

The difference in electrophoretic property of α1-tubulin between S and $R^+$ biotypes may directly or indirectly reflect a difference in the amino acid composition of the α1-tubulin polypeptide. It was concluded that the gene encoding α1-tubulin polypeptide (hereinafter referred to as the α1-tubulin gene) in the $R^+$ biotype has a mutated coding region, relative to that of the S biotype. It was also concluded that dinitroaniline resistance in the $R^+$ biotype is attributable to expression of a modified α1-tubulin gene.

The genetic analysis of dinitroaniline resistance in goosegrass was investigated by the study of F1 plants and F2 seed using pendimethalin as the selective agent. Putative F1hybrids (susceptible S biotype×"40 fold" $R^+$ biotype) showed partial resistance to pendimethalin. Preliminary evaluation of F2 progeny indicated inheritance of dinitroaniline resistance from some of the putative F1 hybrids. A range of seedling phenotypes was obtained form fully sensitive to fully resistant. Initial observations suggest that resistance is not fully dominant, but the segregation data are difficult to interpret. Further F2 families may be evaluated to clarify the inheritance pattern of the dinitroaniline resistance trait. A range of F2 seedlings, classified as susceptible or resistant phenotypes, may be grown to provide F3 families for analysis of genetic linkage between the "shifted" α1-tubulin isotype and the resistance trait.

(Analysis of the segregation pattern in *Setaria viridis* suggests that trifluralin resistance is a recessive (or possibly semi-dominant) trait at one locus).

EXAMPLE 4

Cloning and Sequencing of the DNA Encoding α1-tubulin

The cDNA sequence encoding the modified α1-tubulin isotype in the $R^+$ biotype was cloned by routine recombinant DNA techniques.

(a) Construction of CDNA libraries cDNA libraries were constructed in λUniZAP from poly $[A]^+$ RNA isolated from dark-grown seedlings of susceptible (S) and and "40 fold" resistant ($R^+$) *E indica* biotypes.

Seedlings of the S biotype of goosegrass were germinated on gelled medium for 14 days in darkness. 458 μg of total RNA was obtained from 2.3 g of harvested shoots, and 366 μg of this RNA yielded 3.6 μg poly$[A]^+$ RNA. CDNA synthesised using the Stratagene λZAP kit was size-fractionated on a Sephacryl column, and the two fractions containing the largest cDNAs were used to construct libraries in λUniZAP. cDNA inserts cloned into λUniZAP were directionally orientated by the inclusion of an XhoI site in the poly-T primer used in 1st strand synthesis, and by the addition of EcoRI adaptors to the cDNA. Of a total of $5\times10^5$ phage plaques, 14 were picked at random to estimate the average insert size of this library. 10 of the 14 plaques gave PCR products, of which the average insert size was 1.2 kb (insert size ranged from 0.6 kb to 2.0 kb). A library of $2\times10^5$ phage plaques were produced from the second fraction obtained from the Sephacryl column.

A cDNA library was similarly constructed from dark-grown seedlings of the $R^+$ biotype of goosegrass. 3.04 μg of poly$[A]^+$ RNA was isolated from 532 μg of total RNA and was cloned as cDNA into λUniZAP. cDNA eluted in the first fraction from a Sephacryl spin column was used to produce a library consisting of approximately $4\times10^5$ λ phage. Of 14 plaques analysed by PCR, insert sizes ranged from 0.5 kb to 3.15 kb, with an average insert size of 1.43 kb. $6\times10^4$ pfu were plated and duplicate filter-lifts were prepared.

(b) Library screening

Approximately 0.5% of plaques in each library hybridised to a maize α-tubulin probe, consistent with the anticipated abundance of α-tubulin mRNA in goosegrass seedlings.

$6\times10^4$ pfu (from the $5\times10^5$ S library) were plated and probed using a radiolabelled maize α-tubulin CDNA probe, pMR19 (corresponding to the Zmtual gene). Of approximately 300 plaques which hybridised, 25 were picked for purification to obtain single hybridising plaques. 14 purified plaques retained hybridisation to pMR19. PCR analysis of the phage clones showed insert sizes ranging form 1.5 to 2.0 kb. Direct DNA sequencing of the PCR products was attempted but gave limited and unclear results; 4 species of cDNA appeared to be represented among the phage clones.

One set of filters from the $R^+$ library was also probed with the generic α-tubulin probe (maize pMR19) and this indicated that the frequency of α-tubulin clones observed in the $R^+$ biotype library was similar to that in the S biotype library (ie 0.5%).

(c) Isolation of clones corresponding to the most abundant α-tubulin mRNA species Clones were grouped into α-tubulin family members, based on divergence in the 3' non-coding region. Nucleotide sequence information from the 3' and/or 5' untranslated regions of selected cDNA clones from the S and $R^+$ libraries indicated one highly prevalent α-tubulin species and at least two low abundance α-tubulin species.

Inserts from 11 of the 14 S clones were in vivo excised to allow plasmid sequencing of the cDNA. During this process one of the clones appeared to lose the cDNA insert. DNA sequencing demonstrated that 11 of theideiginal 13 clones have identical 3' regions, indicating these to be the most prevalent α-tubulin cDNA species: this group includes the full-length CDNA clone S#15. The remaining two plaque-purified clones appear to be distinct from the prevalent cDNA species and from each other. One of these low abundance clones, S8, has a nucleotide sequence which resembles that of the maize subfamily III α-tubulin gene (Zmtua3).

In order to isolate a full-length homologue of clone S#15 (ie the prevalent cDNA species in the S biotype library) from the $R^+$ biotype library, the second set of filters was probed with a 94-bp PCR fragment derived from the 5' non-coding region of clone S#15. Clones hybridising to this probe accounted for approximately 80% of all plaques which hybridised to the pMR19 probe. This indicated that the prevalence of the cDNA species observed in the S biotype library was reproduced in the $R^+$ biotype library. Of 3 clones picked for plaque purification, one failed at in vivo excision and one proved to be partial length. Clone $R^+$#2 contained a full-length insert and sequence results from both the 5' and 3' untranslated regions indicated that this cDNA is broadly equivalent to clone S#15.

(d) Characterisation of modified α-tubulin CDNA

The coding regions of the prevalent cDNA species (both strands of clones S#15 and $R^+$#2) have been sequenced. Comparison of S and $R^+$ biotypes revealed an amino acid substitution encoded by the prevalent cDNA species: threonine at position 239 is substituted by isoleucine.

The clone S#15 has been fully sequenced and shows close similarity to maize subfamily I α-tubulin genes (Zmtua1, Zmtua2, Zmtua4) as 95% of the N-terminal amino acids are identical. This subfamily is believed to code for the maize α4-tubulin isotype, which is the most abundant of the α-tubulin gene products in developing tissues. Like maize subfamily I α-tubulins, clone S#15 has a lysine residue at position 40 which is the site of post-translational acetylation (associated with microtubule stability in algae, but not yet observed in plants). Table 5 below shows the DNA sequence of clone S#15 (1652 total bases; composition: 323 A, 494 C, 448 G, 387 T, 0 OTHER).

The coding region of clone $R^+$#2 has also been sequenced, and the nucleotide sequence and encoded amino acid sequence compared with that from S#15. Table 3 above shows the DNA sequence of clone $R^+$#2 (1593 total bases; composition: 312 A, 484 C, 433 G, 364 T, 0 OTHER). Several bases differ between S#15 and $R^+$#2. The most significant sequence difference is the single base change C to T in $R^+$#2 resulting in the amino acid substitution $Thr^{239}$ (threonine predicted by the codon ACA in the S biotype) to $Ile^{239}$ (isoleucine predicted by the codon ATA in the $R^+$ biotype). Sequencing in both directions of the cDNA from either clone confirmed this difference between the biotypes. This mutation has been observed in two independent clones isolated from the $R^+$ cDNA library.

Table 6 is a comparison of the predicted protein sequences from the *E indica* cDNA clones S#15 (sequence ELS15, top row) and $R^+$#2 (sequence ELR2, bottom row).

TABLE 5

DNA SEQUENCE OF CLONE S #15

| | 10 20 30 40 50 |
|---|---|
| 1 | GGAGACAGGCGTCTTCGTACTCGCCTCTCTCCGCGACTCCAAGCTTTCTC |
| 51 | CCTCCTCCCATTTCCCGTCGCCGCCGCCTCACCCGTACGACACCATGAGG |
| 101 | GAGTGCATCTCGATCCACATCGGCCAGGCCGGTATCCAGGTCGGAAACGC |
| 151 | TTGCTGGGAGCTCTACTGCCTCGAGCATGGCATCCAGGCTGACGGTCAGA |
| 201 | TGCCCGGTGACAAGACCATTGGAGGAGGTGATGATGCTTTCAACACCTTC |
| 251 | TTCAGTGAGACTGGCGCCGGCAAGCATGTGCCCCGTGCCGTGTTTGTTGA |
| 301 | CCTTGAGCCCACTGTGATCGATGAGGTCAGGACTGGCACCTACCGCCAGC |
| 351 | TGTTTCACCCTGAGCAGCTCATCAGTGGCAAGGAGGATGCTGCCAACAAC |
| 401 | TTTGCCCGTGGTCACTACACCATTGGCAAGGAGATTGTTGACCTGTGCCT |
| 451 | TGACCGCATCAGGAAGCTTGCCGACAACTGTACTGGTCTCCAGGGCTTCC |
| 501 | TTGTCTTCAACGCTGTCGGTGGAGGAACGGGCTCTGGTCTTGGTTCCCTC |
| 551 | CTCCTTGAGCGCCTGTCTGTTGACTACGGCAAGAAGTCCAAGCTCGGGTT |
| 601 | CACTGTCTACCCGTCTCCTCAGGTCTCCACCTCGGTGGTTGAGCCATACA |

TABLE 5-continued

| | |
|---|---|
| | DNA SEQUENCE OF CLONE S #15 |
| 651 | ACAGTGTGCTGTCCACCCACTCCCTCCTTGAGCACACCGATGTGGCTGTG |
| 701 | CTGCTTGACAACGAGGCCATCTACGACATCTGCCGCCGCTCCCTGGACAT |
| 751 | TGAGCGCCCAACCTACACCAACCTGAACAGGCTTGTTTCTCAGGTCATTT |
| 801 | CATCACTGACAGCCTCTCTGAGGTTCGATGGTGCTCTGAACGTGGATGTG |
| 851 | AACGAGTTCCAGACCAACTTGGTGCCCTACCCGAGGATCCACTTCATGCT |
| 901 | TTCATCCTACGCTCCAGTGATCTCCGCGGAGAAGGCCTACCACGAGCAGC |
| 951 | TGTCCGTGGCTGAGATCACCAACAGCGCGTTCGAGCCTTCCTCCATGATG |
| 1001 | GCCAAGTGCGACCCCCGCCACGGCAAGTACATGGCCTGCTGCCTCATGTA |
| 1051 | CCGTGGTGATGTGGTGTCCAAGGACGTGAACGCTGCCGTTGCCACCATCA |
| 1101 | AGACCAAGCGCACCATCCAGTTCGTGGACTGGTGCCCCACTGGCTTCAAG |
| 1151 | TGCGGTATCAACTACCAGCCACCCAGCGTCGTCCCCGGCGGCGACCTGGC |
| 1201 | CAAGGTGCAGAGGGCCGTGTGCATGATCTCCAACTCCACCAGTGTCGTCG |
| 1251 | AGGTGTTCTCCCGCATCGACCACAAGTTCGACCTCATGTACGCCAAGCGC |
| 1301 | GCCTTCGTCCACTGGTACGTGGGTGAGGGTATGGAGGAGGGTGAGTTCTC |
| 1351 | CGAGGCGCGTGAGGACCTTGCTGCCCTTGAGAAGGACTACGAGGAGGTCG |
| 1401 | GCGCTGAGTTCGACGAGGGTGAGGAAGGTGATGAGGGTGACGAGTACTAG |
| 1451 | ATGAATCTACGCTTCCTGCTGTTGTGTCAGGCCTGTGTGCCGCTGCTATC |
| 1501 | CTGTGATCTGCCCGAGGGCGCTATCGTGTCGTGTCAGTTTGAACTATTTG |
| 1551 | TCATTGTGTGGTTACAACCCCTGAAGTTGTAGACATGTTTAATTCCCGCT |
| 1601 | TTGCTACTGGGTTATCAACATCGTTATGTTTGTCTAAAAAAAAAAAAAAA |
| 1651 | AA |

TABLE 6

```
ELS15-M R E C I S I H I G Q A G I Q V G N A C W E L Y C L E H G I Q A D G Q M P G D K T I G G G D D A F N T F F S E -55
      * * * * * * * * * * * * * * * * * * * * * * * * * * * * * * * * * * * * * * * * * * * * * * * * * * * * * * *
ELR2 -M R E C I S I H I G Q A G I Q V G N A C W E L Y C L E H G I Q A D G Q M P G D K T I G G G D D A F N T F F S E -55

ELS15-T G A G K H V P R A V F V D L E P T V I D E V R T G T Y R Q L F H P E Q L I S G K E D A A N N F A R G H Y T I -110
      * * * * * * * * * * * * * * * * * * * * * * * * * * * * * * * * * * * * * * * * * * * * * * * * * * * * * * *
ELR2 -T G A G K H V P R A V F V D L E P T V I D E V R T G T Y R Q L F H P E Q L I S G K E D A A N N F A R G H Y T I -110

ELS15-G K E I V D L C L D R I R K L A D N C T G L Q G F L V F N A V G G G T G S G L G S L L L E R L S V D Y G K K S -165
      * * * * * * * * * * * * * * * * * * * * * * * * * * * * * * * * * * * * * * * * * * * * * * * * * * * * * * *
ELR2 -G K E I V D L C L D R I R K L A D N C T G L Q G F L V F N A V G G G T G S G L G S L L L E R L S V D Y G K K S -165

ELS15-K L G F T V Y P S P Q V S T S V V E P Y N S V L S T H S L L E H T D V A I L L D N E A I Y D I C R R S L D I E -220
      * * * * * * * * * * * * * * * * * * * * * * * * * * * * * * * * * * * * * * * * * * * * * * * * * * * * * * *
ELR2 -K L G F T V Y P S P Q V S T S V V E P Y N S V L S T H S L L E H T D V A I L L D N E A I Y D I C R R S L D I E -220

ELS15-R P T Y T N L N R L V S Q V I S S L T A S L R F D G A L K V D V N E F Q D N L V P Y P R I H F M L S S Y A P V -275
      * * * * * * * * * * * * * * * * * *   * * * * * * * * * * * * * * * * * * * * * * * * * * * * * * * * * * * *
ELR2 -R P T Y T N L N R L V S Q V I S S L I A S L R F D G A L K V D V N E F Q D N L V P Y P R I H F M L S S Y A P V -275

ELS15-I S A E K A Y H E Q L S V A E I T N S A F E P S S M M A K C D P R H G K Y M A C C L M Y R G D V V P K D V N A -330
      * * * * * * * * * * * * * * * * * * * * * * * * * * * * * * * * * * * * * * * * * * * * * * * * * * * * * * *
ELR2 -I S A E K A Y H E Q L S V A E I T N S A F E P S S M M A K C D P R H G K Y M A C C L M Y R G D V V P K D V N A -330

ELS15-A V A T I K T K R T I Q F V D W C P T G F K C G I N Y Q P P S V V P G G D L A K V Q R A V C M I S N S T S V V -385
      * * * * * * * * * * * * * * * * * * * * * * * * * * * * * * * * * * * * * * * * * * * * * * * * * * * * * * *
ELR2 -A V A T I K T K R T I Q F V D W C P T G F K C G I N Y Q P P S V V P G G D L A K V Q R A V C M I S N S T S V V -385

ELS15-E V F S R I D H K F D L M Y A K R A F V H W Y V G E G M E E G E F S E A R E D L A A L E K D Y E E V G A E F D -440
      * * * * * * * * * * * * * * * * * * * * * * * * * * * * * * * * * * * * * * * * * * * * * * * * * * * * * * *
ELR2 -E V F S R I D H K F D L M Y A K R A F V H W Y V G E G M E E G E F S E A R E D L A A L E K D Y E E V G A E F D -440
```

TABLE 6-continued

| |
|---|
| ELS15-E G E E G D E G D E Y-451 |
| * * * * * * * * * * * |
| ELR2 -E G E E G D E G D E Y-451 |

The DNA sequence difference in the coding region predicts a modified amino acid sequence of α1-tubulin between the two biotypes. The substitution of Thr with Ile replaces a polar residue (—$C_2H_4OH$) with a non-polar residue ($C_4H_9$). This non-conservative substitution may directly change the electrophoretic properties of the tubulin polypeptide (as resolved by 2-D gel analysis) and/or may subtly alter the conformation of the α-tubulin polypeptide such that it becomes a target for post-translational acetylation (associated with microtubule stability, and detectable as an electrophoretic shift). Thus the $R^+$#2 CDNA apparently corresponds to the electrophoretic variant α1-tubulin shown to be present in the $R^+$ biotype.

Confirmation that the CDNA clone $R^+$#2 encodes the α1-tubulin polypeptide of the $R^+$ biotype may be obtained in two ways.

One approach is to raise isotype-specific antibodies to synthetic oligopeptides corresponding to variable coding regions of the α-tubulin CDNA clones. The identification of an antibody which specifically reacts with α1-tubulin isotype pin-points the corresponding CDNA.

A second approach is to use the different CDNA clones as gene-specific hybridisation probes on genomic DNA extracted from F2 progeny derived from selfing a S×$R^+$ F1 hybrid. The genomic DNA is cut with restriction enzymes to display the α-tubulin genes as restriction fragment length polymorphisms (RFLPS) within each biotype and between the S and $R^+$ biotypes. Examination of the F2 population allows genetic linkage to be assigned between the resistance trait, the modified α1-tubulin isotype, and a specific α-tubulin genomic restriction fragment. The $R^+$ biotype CDNA clone specifically hybridising with this resistance-linked restriction fragment corresponds to the α1-tubulin isotype.

EXAMPLE 5

Identification of the Gene Encoding the α1-Tubulin Isotype

A gene-specific probe may be constructed from the clone S#15 and from the clone $R^+$#2 (the α1-tubulin cDNA) and used to identify the homologous gene from a genomic DNA library of the corresponding biotype.

PCR products obtained from both S and $R^+$ genomic DNA have been cloned and sequenced. Comparison of the genomic and CDNA sequences has confirmed that the base change is not an artefact of the cDNA cloning procedure and is present within the gene from which the mRNA for clone $R^+$#2 was transcribed.

The genomic sequences contain an intron of approximately 110 bp in a position identical to that observed in two tandemly arranged maize α-tubulin genes.

EXAMPLE 6

Construction of maize expression vectors containing α1-tubulin CDNA

The α1-tubulin CDNA with the $Ile^{239}$ substitution ($R^+$#2) has been cloned into an expression vector for transformation into a maize cell line.

The following two pairs of vectors have been constructed. To demonstrate linkage of the herbicide resistance trait to the α1-tubulin cDNA, the vectors are used to transform BMS maize cells (using any suitable DNA delivery technique such as bombardment or electroporation) and dinitroaniline resistance is measured in the undifferentiated culture tissue. The vectors allow two regimes of selection according to their structure:

(i) Vectors for transformation and initial selection on bialaphos followed by dinitroaniline

VECTOR PBTS

CaMV35S-Adhi1/S#15 ORF/Nos—CaMV35S-Adhi1/bar/Nos—(pUC)

VECTOR pBTR+

CaMV35S-Adhi1/$R^+$#2 ORF/Nos—CaMV35S-Adhi1/bar/Nos—(pUC)

(ii) Vectors for transformation and direct selection using a dinitroaniline (pendimethalin or trifluralin)

VECTOR pGTS

CaMV35S-Adhi1/GUS/CaMV35S—CaMV35S-Adhi1/S#15 ORF/Nos—(pUC)

VECTOR pGTR+

CaMV35S-Adhi1/GUS/CaMV35S—CaMV35S-Adhi1/$R^+$#2 ORF/Nos—(pUC)

Figure 7:
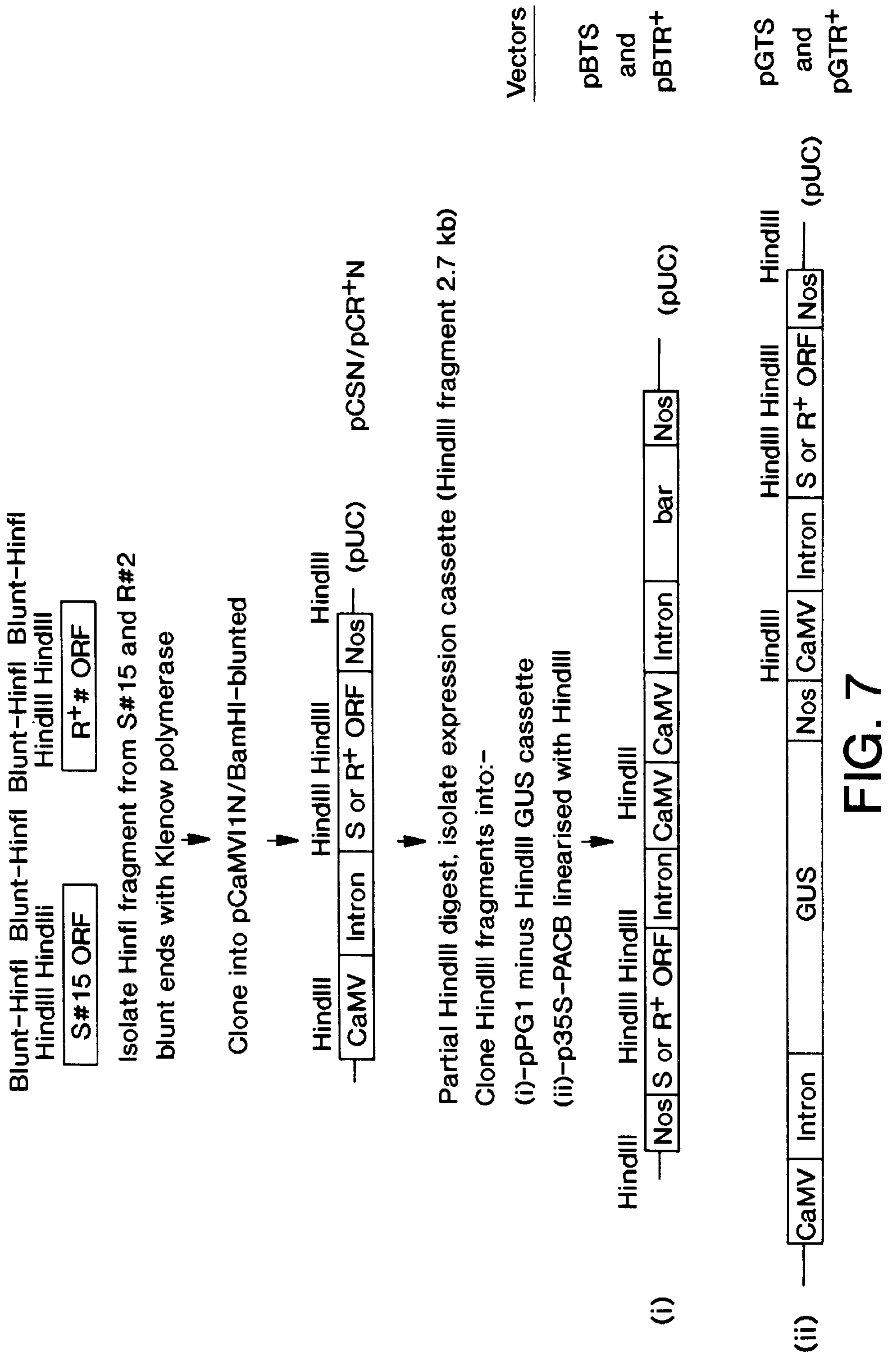
FIG. 7 is a diagram showing the construction of vectors for maize transformation.

FIG. 7 is a diagram showing the construction of these vectors for maize cell line transformation. The S#15 and $R^+$#2 α1-tubulin expression cassettes were constructed using a 1.4 kb Hinf I fragment containing the complete coding region predicted by the cDNA sequence. The fragments were isolated, blunt ended and cloned between the CaMV35S-Adhi1promoter and Nos 3' end in pCaMVI1N/Bam(blunt). The resulting plasmids (pCSN and pC$R^+$N) were sequenced and restriction mapped to confirm the orientation and integrity of the ORFs. The pCSN and pC$R^+$N expression cassettes were partially digested to yield a 2.7 kb Hind III fragment. The fragment was isolated and cloned into pPG1(minus GUS) resulting in vectors of type (i) and into p35S-PACB resulting in vectors of type (ii).

Figure 8:
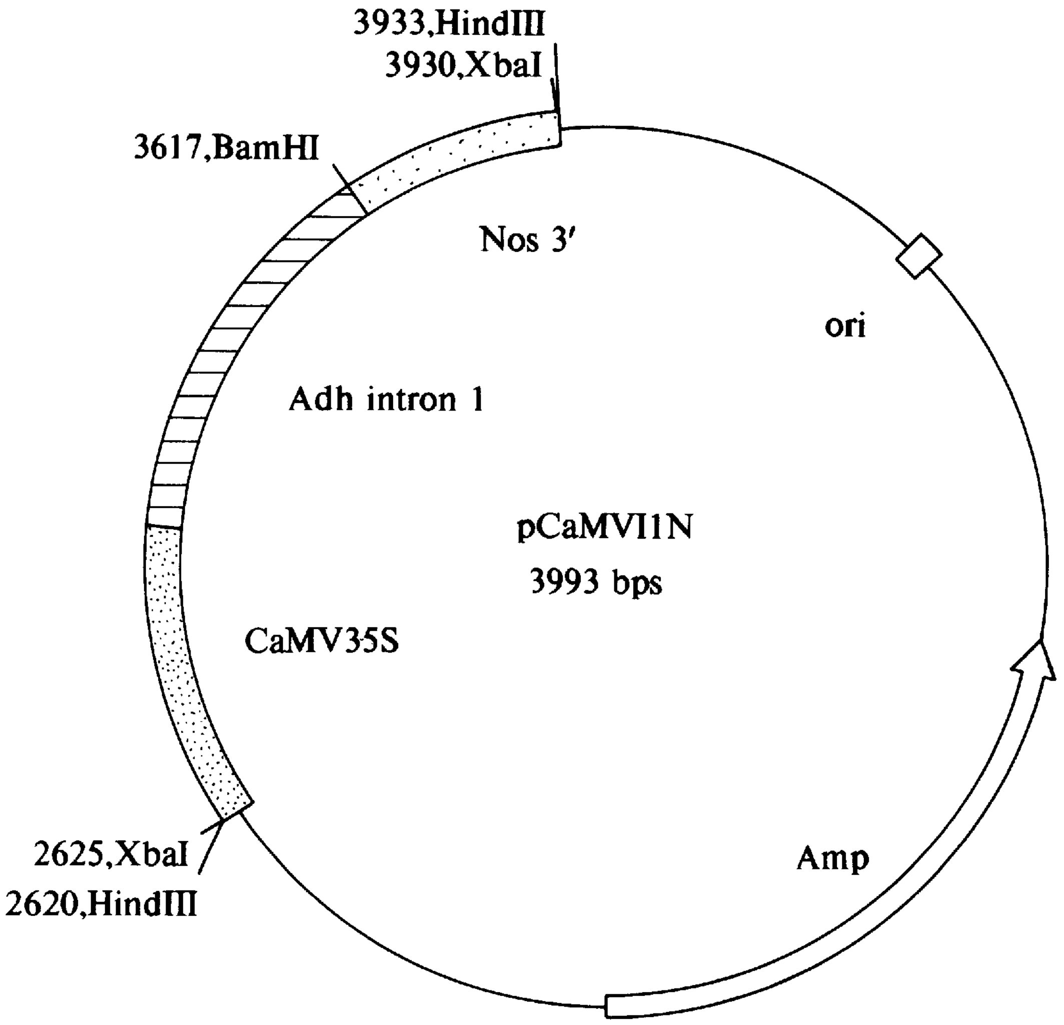
FIG. 8 is a diagram showing the structure of the vector pCaMvI1N.
Figure 9:
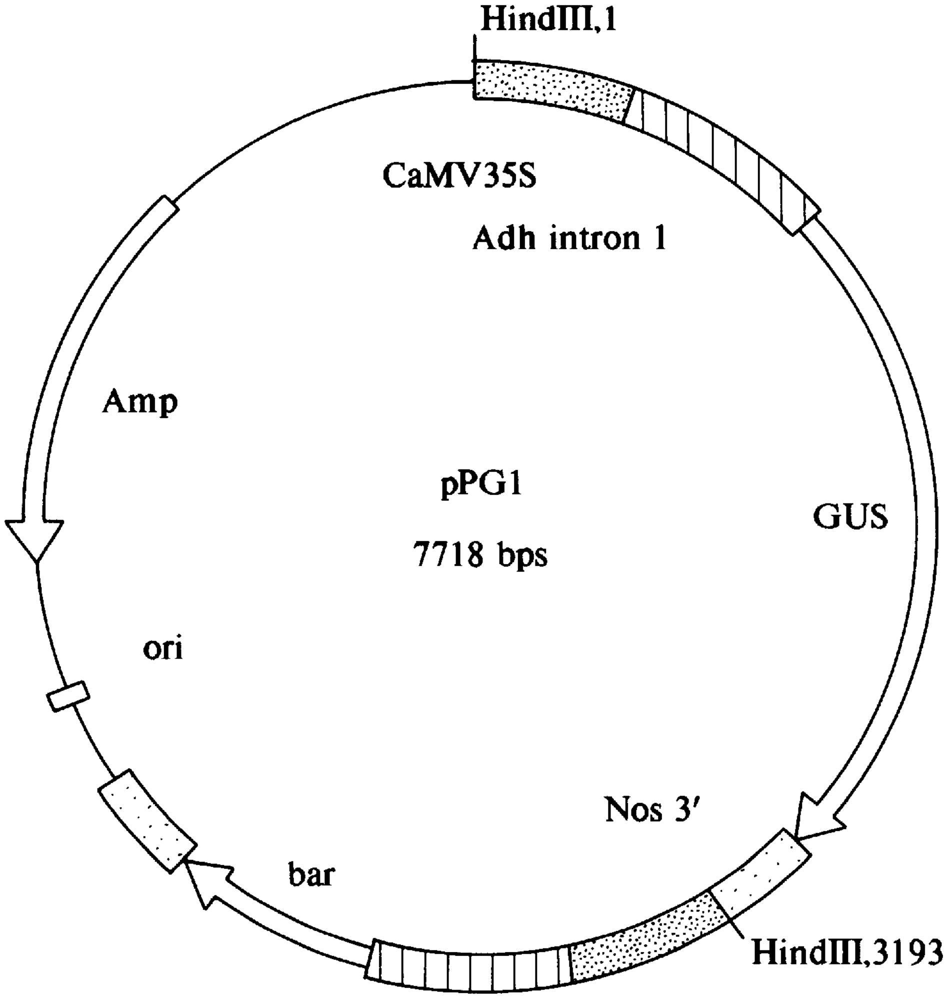
FIG. 9 is a diagram showing the structure of the vector pPG1.
Figure 10:
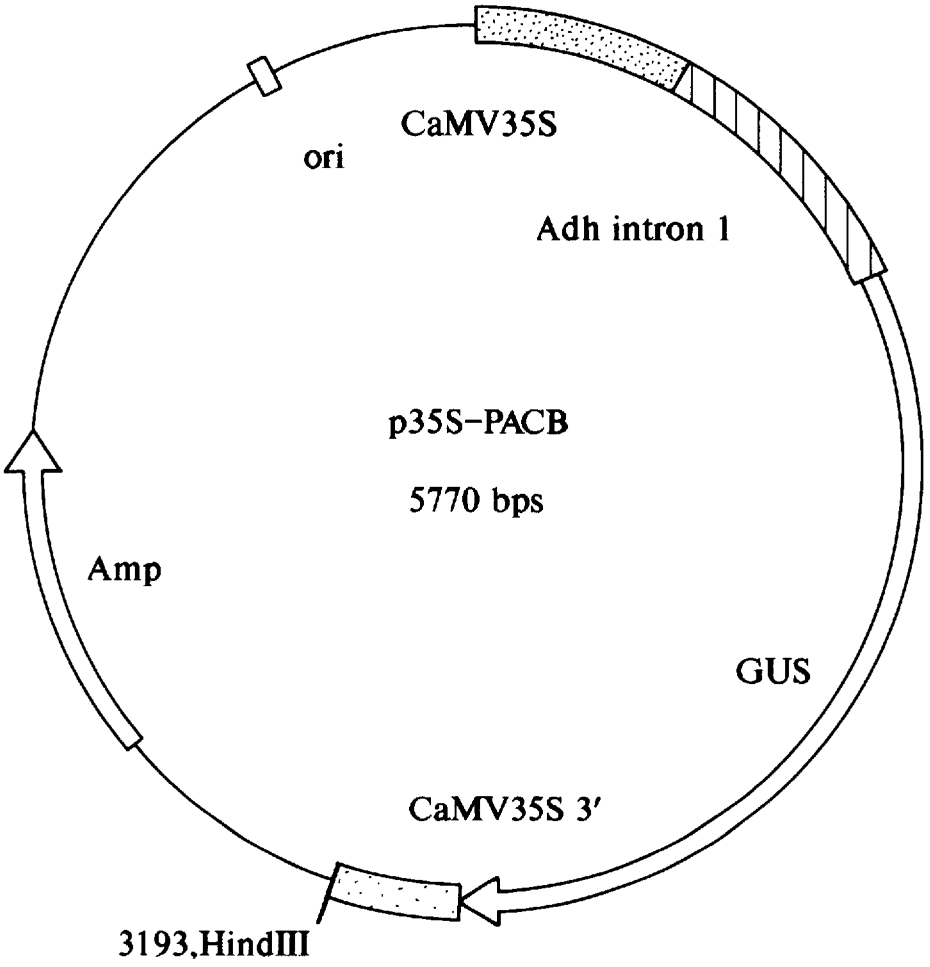
FIG. 10 is a diagram showing the structure of the vector p35SPACB.

FIGS. 8, 9 and 10 show the detailed structure of the vectors pCaMVI1N, pPG1 and p35SPACB respectively.

We claim:

1. An isolated DNA encoding an α- or γ- tubulin, which tubulin is resistant to an anti-tubulin agent selected from the group consisting of dinitroanaline, phosphorothioamidate and chlorthal dimethyl, the resistant tubulin comprising a non-polar amino acid instead of a threonine residue at a position corresponding to that depicted as position 239, 237, or 240 in Table 2.

2. The isolated DNA of claim 1, wherein the non-polar amino acid is selected from the group consisting of isoleucine, leucine and valine.

3. The isolated DNA as claimed in claim 2, wherein the non-polar amino acid is isoleucine.

4. The isolated DNA as claimed in claim 1, which has an amino acid substitution at position 239 of the α-tubulin sequence shown in Table 2.

5. The isolated DNA as claimed in claim 1 which has an amino substitution at position 240 of the γ-tubulin sequence shown in Table 2.

6. The isolated DNA as claimed in claim 1, in which the DNA sequence corresponds to the sequence shown in Table 3.

7. The isolated DNA as claimed in claim 1, which is isolated from the clone R+#2 deposited at The National Collections of Industrial and Marine Bacteria on 24 May 1993 under the accession number NCIMB 40558.

8. The isolated DNA as claimed in claim 1, in which the DNA sequence is isolated from an *Eleusine indica* biotype deposited at The National Collections of Industrial and Marine Bacteria on 11 May 1992 under the accession number NCIMB 40504.

9. The isolated DNA as claimed in claim 1, which encodes the sequence ELR2 depicted in Table 6.

10. The isolated DNA as claimed in claim 1, in which the DNA sequence is preceded by a transcriptional initiation region operative in a biological cell so that a construct containing said DNA sequence can generate mRNA in the cell.

11. A method of producing a plant cell resistant to an anti-tubulin agent comprising transformation of a cell of the plant with the isolated DNA as claimed in claim 1 and selecting from the thus transformed material that which is resistant to a herbicide selected from the group consisting of dinitroanaline, phosphorothioamidate and chlorthal dimethyl.

12. A transgenic cell containing the isolated DNA of claim 1.

13. A transgenic plant cell according to claim 12, which is a plant cell.

* * * * *

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
( A ) LENGTH: 37 amino acids
( B ) TYPE: amino acid
( C ) STRANDEDNESS: single
( D ) TOPOLOGY: linear ( i i ) MOLECULE TYPE: protein ( v i ) ORIGINAL SOURCE:
( A ) ORGANISM: TABLE 2 ALPHA-TUBULIN AA SEQUENCE ( x i ) SEQUENCE DESCRIPTION: SEQ ID NO:1:

Arg Pro Thr Tyr Thr Asn Leu Asn Arg Leu Ile Ala Gln Val Val Ser
1 5 10 15

Ser Ile Thr Ala Ser Leu Arg Phe Asp Gly Ala Leu Asn Val Asp Leu
20 25 30

Thr Glu Phe Gln Thr
35

( 2 ) INFORMATION FOR SEQ ID NO:2:

( i ) SEQUENCE CHARACTERISTICS:
( A ) LENGTH: 37 amino acids
( B ) TYPE: amino acid
( C ) STRANDEDNESS: single
( D ) TOPOLOGY: linear ( i i ) MOLECULE TYPE: protein ( v i ) ORIGINAL SOURCE:
( A ) ORGANISM: TABLE 2 BETA-TUBULIN AA SEQUENCE ( x i ) SEQUENCE DESCRIPTION: SEQ ID NO:2:

Thr Pro Thr Tyr Gly Asp Leu Asn His Leu Val Ser Ala Thr Met Ser
1 5 10 15

Gly Val Thr Thr Cys Leu Arg Phe Pro Gly Gln Leu Asn Ala Asp Leu
20 25 30

Arg Lys Leu Ala Val
35

( 2 ) INFORMATION FOR SEQ ID NO:3:

( i ) SEQUENCE CHARACTERISTICS:
( A ) LENGTH: 37 amino acids
( B ) TYPE: amino acid
( C ) STRANDEDNESS: single
( D ) TOPOLOGY: linear ( i i ) MOLECULE TYPE: protein ( v i ) ORIGINAL SOURCE:
( A ) ORGANISM: TABLE 2 GAMMA-TUBULIN AA SEQUENCE ( x i ) SEQUENCE DESCRIPTION: SEQ ID NO:3:

Asn Pro Ser Phe Ser Gln Ile Asn Gln Leu Val Ser Thr Ile Met Ser
1 5 10 15

Ala Ser Thr Thr Thr Leu Arg Tyr Pro Gly Tyr Met Asn Asn Asp Leu
20 25 30

Ile Gly Ile Ile Ala

35

(2) INFORMATION FOR SEQ ID NO:4:

(i) SEQUENCE CHARACTERISTICS:
(A) LENGTH: 21 amino acids
(B) TYPE: amino acid
(C) STRANDEDNESS: single
(D) TOPOLOGY: linear (ii) MOLECULE TYPE: protein (vi) ORIGINAL SOURCE:
(A) ORGANISM: TABLE 2 CONSENSUS AA SEQUENCE (xi) SEQUENCE DESCRIPTION: SEQ ID NO:4:

Pro Thr Tyr Leu Asn Leu Val Ser Met Ser Thr Thr Leu Arg Phe Pro
1 5 10 15

Gly Leu Asn Asp Leu
20

(2) INFORMATION FOR SEQ ID NO:5:

(i) SEQUENCE CHARACTERISTICS:
(A) LENGTH: 5 amino acids
(B) TYPE: amino acid
(C) STRANDEDNESS: single
(D) TOPOLOGY: linear (ii) MOLECULE TYPE: protein (vi) ORIGINAL SOURCE:
(A) ORGANISM: TABLE 2 IDENTITY (xi) SEQUENCE DESCRIPTION: SEQ ID NO:5:

Pro Leu Thr Arg Asn
1 5

(2) INFORMATION FOR SEQ ID NO:6:

(i) SEQUENCE CHARACTERISTICS:
(A) LENGTH: 1593 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: TABLE 3 R+2

(xi) SEQUENCE DESCRIPTION: SEQ ID NO:6:

CTCGCCTCTC TCCGCGACTC CAAGCTTTCT CCCTCCTCCC ATTTCCCGTC GCCGCCGCCT 60

CACCCGCCCG ACACCATGAG GGAGTGCATC TCGATCCACA TCGGCCAGGC CGGTATCCAG 120

GTCGGAAACG CTTGCTGGGA GCTCTACTGC CTCGAGCATG GCATCCAGGC TGACGGTCAG 180

ATGCCCGGTG ACAAGACCAT TGGAGGAGGT GATGATGCTT TCAACACCTT CTTCAGTGAG 240

ACTGGCGCCG GCAAGCATGT GCCCCGTGCC GTGTTTGTTG ACCTTGAGCC CACTGTGATC 300

GATGAGGTCA GGACTGGCAC CTACCGCCAG CTGTTTCACC CTGAGCAGCT CATCAGTGGC 360

AAGGAGGATG CTGCCAACAA CTTTGCCCGT GGTCACTACA CCATTGGCAA GGAGATTGTT 420

GACCTGTGCC TTGACCGCAT CAGGAAGCTT GCCGACAACT GTACTGGTCT CCAGGGCTTC 480

CTTGTCTTCA ACGCTGTCGG TGGAGGAACG GGCTCTGGTC TTGGTTCCCT CCTCCTTGAG 540

CGCCTGTCTG TTGACTACGG CAAGAAGTCC AAGCTCGGGT TCACTGTCTA CCCGTCTCCC 600

CAGGTCTCCA CCTCGGTGGT TGAGCCATAC AACAGTGTGC TGTCCACCCA CTCCCTCCTT 660

```
GAGCACACCG ATGTGGCTGT GCTGCTTGAC AACGAGGCCA TCTACGACAT CTGCCGCCGC    720
TCCCTGGACA TTGAGCGCCC AACCTACACC AACCTGAACA GGCTTGTTTC TCAGGTCATT    780
TCATCACTGA TAGCCTCTCT GAGGTTCGAT GGTGCTCTGA ACGTGGATGT GAACGAGTTC    840
CAGACCAACT TGGTGCCCTA CCCGAGGATC CACTTCATGC TTTCATCCTA CGCTCCAGTG    900
ATCTCCGCGG AGAAGGCCTA CCACGAGCAG CTGTCCGTGG CTGAGATCAC CAACAGCGCG    960
TTCGAGCCTT CCTCCATGAT GGCCAAGTGC GACCCCCGCC ACGGCAAGTA CATGGCCTGC   1020
TGCCTCATGT ACCGTGGTGA TGTGGTGTCC AAGGACGTGA ACGCCGCCGT TGCCACCATC   1080
AAGACCAAGC GCACCATCCA GTTCGTGGAC TGGTGCCCCA CTGGCTTCAA GTGCGGTATC   1140
AACTACCAGC CACCCAGCGT CGTCCCCGGC GGCGACCTGG CCAAGGTGCA GAGGGCCGTG   1200
TGCATGATCT CCAACTCCAC CAGTGTCGTC GAGGTGTTCT CCCGCATCGA CCACAAGTTC   1260
GACCTCATGT ACGCCAAGCG CGCCTTCGTC CACTGGTACG TGGGTGAGGG TATGGAGGAG   1320
GGTGAGTTCT CCGAGGCGCG TGAGGACCTT GCTGCCCTTG AGAAGGACTA CGAGGAGGTC   1380
GGCGCTGAGT TCGACGAGGG TGAGGAAGGT GATGAGGGTG ACGAGTACTA GATGAATCTA   1440
CGCTTCCTGC TGTTGTGTCA GGCCTGTGTG CCGCTGCTAT CCTGTGATCT GCCCGAGGGC   1500
GCTATCGTGT CGTGTCAGTT TGAACTATTT GTCATTGTGT GGTTACAACC CCTGAAGTTG   1560
TAGACATGTT TAATTCAAAA AAAAAAAAAA AAA                                1593
```

( 2 ) INFORMATION FOR SEQ ID NO:7:

( i ) SEQUENCE CHARACTERISTICS:
( A ) LENGTH: 1652 base pairs
( B ) TYPE: nucleic acid
( C ) STRANDEDNESS: single
( D ) TOPOLOGY: linear ( i i ) MOLECULE TYPE: cDNA ( v i ) ORIGINAL SOURCE:
( A ) ORGANISM: TABLE 5 S15

( x i ) SEQUENCE DESCRIPTION: SEQ ID NO:7:

```
GGAGACAGGC GTCTTCGTAC TCGCCTCTCT CCGCGACTCC AAGCTTTCTC CCTCCTCCCA     60
TTTCCCGTCG CCGCCGCCTC ACCCGTACGA CACCATGAGG GAGTGCATCT CGATCCACAT    120
CGGCCAGGCC GGTATCCAGG TCGGAAACGC TTGCTGGGAG CTCTACTGCC TCGAGCATGG    180
CATCCAGGCT GACGGTCAGA TGCCCGGTGA CAAGACCATT GGAGGAGGTG ATGATGCTTT    240
CAACACCTTC TTCAGTGAGA CTGGCGCCGG CAAGCATGTG CCCCGTGCCG TGTTTGTTGA    300
CCTTGAGCCC ACTGTGATCG ATGAGGTCAG GACTGGCACC TACCGCCAGC TGTTTCACCC    360
TGAGCAGCTC ATCAGTGGCA AGGAGGATGC TGCCAACAAC TTTGCCCGTG GTCACTACAC    420
CATTGGCAAG GAGATTGTTG ACCTGTGCCT TGACCGCATC AGGAAGCTTG CCGACAACTG    480
TACTGGTCTC CAGGGCTTCC TTGTCTTCAA CGCTGTCGGT GGAGGAACGG GCTCTGGTCT    540
TGGTTCCCTC CTCCTTGAGC GCCTGTCTGT TGACTACGGC AAGAAGTCCA AGCTCGGGTT    600
CACTGTCTAC CCGTCTCCTC AGGTCTCCAC CTCGGTGGTT GAGCCATACA ACAGTGTGCT    660
GTCCACCCAC TCCCTCCTTG AGCACACCGA TGTGGCTGTG CTGCTTGACA ACGAGGCCAT    720
CTACGACATC TGCCGCCGCT CCCTGGACAT TGAGCGCCCA ACCTACACCA ACCTGAACAG    780
GCTTGTTTCT CAGGTCATTT CATCACTGAC AGCCTCTCTG AGGTTCGATG GTGCTCTGAA    840
CGTGGATGTG AACGAGTTCC AGACCAACTT GGTGCCCTAC CCGAGGATCC ACTTCATGCT    900
TTCATCCTAC GCTCCAGTGA TCTCCGCGGA GAAGGCCTAC CACGAGCAGC TGTCCGTGGC    960
```

```
TGAGATCACC AACAGCGCGT TCGAGCCTTC CTCCATGATG GCCAAGTGCG ACCCCCGCCA 1020
CGGCAAGTAC ATGGCCTGCT GCCTCATGTA CCGTGGTGAT GTGGTGTCCA AGGACGTGAA 1080
CGCTGCCGTT GCCACCATCA AGACCAAGCG CACCATCCAG TTCGTGGACT GGTGCCCCAC 1140
TGGCTTCAAG TGCGGTATCA ACTACCAGCC ACCCAGCGTC GTCCCCGGCG GCGACCTGGC 1200
CAAGGTGCAG AGGGCCGTGT GCATGATCTC CAACTCCACC AGTGTCGTCG AGGTGTTCTC 1260
CCGCATCGAC CACAAGTTCG ACCTCATGTA CGCCAAGCGC GCCTTCGTCC ACTGGTACGT 1320
GGGTGAGGGT ATGGAGGAGG GTGAGTTCTC CGAGGCGCGT GAGGACCTTG CTGCCCTTGA 1380
GAAGGACTAC GAGGAGGTCG GCGCTGAGTT CGACGAGGGT GAGGAAGGTG ATGAGGGTGA 1440
CGAGTACTAG ATGAATCTAC GCTTCCTGCT GTTGTGTCAG GCCTGTGTGC CGCTGCTATC 1500
CTGTGATCTG CCCGAGGGCG CTATCGTGTC GTGTCAGTTT GAACTATTTG TCATTGTGTG 1560
GTTACAACCC CTGAAGTTGT AGACATGTTT AATTCCCGCT TTGCTACTGG GTTATCAACA 1620
TCGTTATGTT TGTCTAAAAA AAAAAAAAAA AA 1652
```

(2) INFORMATION FOR SEQ ID NO:8:

(i) SEQUENCE CHARACTERISTICS:
- (A) LENGTH: 451 amino acids
- (B) TYPE: amino acid
- (C) STRANDEDNESS: single
- (D) TOPOLOGY: linear (ii) MOLECULE TYPE: protein (vi) ORIGINAL SOURCE:
- (A) ORGANISM: TABLE 6 ELS15

(xi) SEQUENCE DESCRIPTION: SEQ ID NO:8:

```
Met Arg Glu Cys Ile Ser Ile His Ile Gly Gln Ala Gly Ile Gln Val
1               5                   10                  15

Gly Asn Ala Cys Trp Glu Leu Tyr Cys Leu Glu His Gly Ile Gln Ala
            20                  25                  30

Asp Gly Gln Met Pro Gly Asp Lys Thr Ile Gly Gly Gly Asp Asp Ala
        35                  40                  45

Phe Asn Thr Phe Phe Ser Glu Thr Gly Ala Gly Lys His Val Pro Arg
    50                  55                  60

Ala Val Phe Val Asp Leu Glu Pro Thr Val Ile Asp Glu Val Arg Thr
65                  70                  75                  80

Gly Thr Tyr Arg Gln Leu Phe His Pro Glu Gln Leu Ile Ser Gly Lys
                85                  90                  95

Glu Asp Ala Ala Asn Asn Phe Ala Arg Gly His Tyr Thr Ile Gly Lys
            100                 105                 110

Glu Ile Val Asp Leu Cys Leu Asp Arg Ile Arg Lys Leu Ala Asp Asn
        115                 120                 125

Cys Thr Gly Leu Gln Gly Phe Leu Val Phe Asn Ala Val Gly Gly Gly
    130                 135                 140

Thr Gly Ser Gly Leu Gly Ser Leu Leu Leu Glu Arg Leu Ser Val Asp
145                 150                 155                 160

Tyr Gly Lys Lys Ser Lys Leu Gly Phe Thr Val Tyr Pro Ser Pro Gln
                165                 170                 175

Val Ser Thr Ser Val Val Glu Pro Tyr Asn Ser Val Leu Ser Thr His
            180                 185                 190

Ser Leu Leu Glu His Thr Asp Val Ala Ile Leu Leu Asp Asn Glu Ala
        195                 200                 205
```

-continued

```
Ile Tyr Asp Ile Cys Arg Arg Ser Leu Asp Ile Glu Arg Pro Thr Tyr
    210                 215                 220

Thr Asn Leu Asn Arg Leu Val Ser Gln Val Ile Ser Ser Leu Thr Ala
225                 230                 235                 240

Ser Leu Arg Phe Asp Gly Ala Leu Lys Val Asp Val Asn Glu Phe Gln
                245                 250                 255

Asp Asn Leu Val Pro Tyr Pro Arg Ile His Phe Met Leu Ser Ser Tyr
            260                 265                 270

Ala Pro Val Ile Ser Ala Glu Lys Ala Tyr His Glu Gln Leu Ser Val
        275                 280                 285

Ala Glu Ile Thr Asn Ser Ala Phe Glu Pro Ser Ser Met Met Ala Lys
    290                 295                 300

Cys Asp Pro Arg His Gly Lys Tyr Met Ala Cys Cys Leu Met Tyr Arg
305                 310                 315                 320

Gly Asp Val Val Pro Lys Asp Val Asn Ala Ala Val Ala Thr Ile Lys
                325                 330                 335

Thr Lys Arg Thr Ile Gln Phe Val Asp Trp Cys Pro Thr Gly Phe Lys
            340                 345                 350

Cys Gly Ile Asn Tyr Gln Pro Pro Ser Val Val Pro Gly Gly Asp Leu
        355                 360                 365

Ala Lys Val Gln Arg Ala Val Cys Met Ile Ser Asn Ser Thr Ser Val
    370                 375                 380

Val Glu Val Phe Ser Arg Ile Asp His Lys Phe Asp Leu Met Tyr Ala
385                 390                 395                 400

Lys Arg Ala Phe Val His Trp Tyr Val Gly Glu Gly Met Glu Glu Gly
                405                 410                 415

Glu Phe Ser Glu Ala Arg Glu Asp Leu Ala Ala Leu Glu Lys Asp Tyr
            420                 425                 430

Glu Glu Val Gly Ala Glu Phe Asp Glu Gly Glu Glu Gly Asp Glu Gly
        435                 440                 445

Asp Glu Tyr
    450
```

( 2 ) INFORMATION FOR SEQ ID NO:9:

( i ) SEQUENCE CHARACTERISTICS:
( A ) LENGTH: 451 amino acids
( B ) TYPE: amino acid
( C ) STRANDEDNESS: single
( D ) TOPOLOGY: linear ( i i ) MOLECULE TYPE: protein ( v i ) ORIGINAL SOURCE:
( A ) ORGANISM: TABLE 6 ELR2

( x i ) SEQUENCE DESCRIPTION: SEQ ID NO:9:

```
Met Arg Glu Cys Ile Ser Ile His Ile Gly Gln Ala Gly Ile Gln Val
1               5                   10                  15

Gly Asn Ala Cys Trp Glu Leu Tyr Cys Leu Glu His Gly Ile Gln Ala
            20                  25                  30

Asp Gly Gln Met Pro Gly Asp Lys Thr Ile Gly Gly Gly Asp Asp Ala
        35                  40                  45

Phe Asn Thr Phe Phe Ser Glu Thr Gly Ala Gly Lys His Val Pro Arg
    50                  55                  60

Ala Val Phe Val Asp Leu Glu Pro Thr Val Ile Asp Glu Val Arg Thr
65                  70                  75                  80

Gly Thr Tyr Arg Gln Leu Phe His Pro Glu Gln Leu Ile Ser Gly Lys
```

-continued

| | | | | 85 | | | | | 90 | | | | | 95 | |
|---|---|---|---|---|---|---|---|---|---|---|---|---|---|---|---|
| Glu | Asp | Ala | Ala | Asn | Asn | Phe | Ala | Arg | Gly | His | Tyr | Thr | Ile | Gly | Lys |
| | | | 100 | | | | | 105 | | | | | 110 | | |
| Glu | Ile | Val | Asp | Leu | Cys | Leu | Asp | Arg | Ile | Arg | Lys | Leu | Ala | Asp | Asn |
| | | 115 | | | | | 120 | | | | | 125 | | | |
| Cys | Thr | Gly | Leu | Gln | Gly | Phe | Leu | Val | Phe | Asn | Ala | Val | Gly | Gly | Gly |
| | 130 | | | | | 135 | | | | | 140 | | | | |
| Thr | Gly | Ser | Gly | Leu | Gly | Ser | Leu | Leu | Leu | Glu | Arg | Leu | Ser | Val | Asp |
| 145 | | | | | 150 | | | | | 155 | | | | | 160 |
| Tyr | Gly | Lys | Lys | Ser | Lys | Leu | Gly | Phe | Thr | Val | Tyr | Pro | Ser | Pro | Gln |
| | | | | 165 | | | | | 170 | | | | | 175 | |
| Val | Ser | Thr | Ser | Val | Val | Glu | Pro | Tyr | Asn | Ser | Val | Leu | Ser | Thr | His |
| | | | 180 | | | | | 185 | | | | | 190 | | |
| Ser | Leu | Leu | Glu | His | Thr | Asp | Val | Ala | Ile | Leu | Leu | Asp | Asn | Glu | Ala |
| | | 195 | | | | | 200 | | | | | 205 | | | |
| Ile | Tyr | Asp | Ile | Cys | Arg | Arg | Ser | Leu | Asp | Ile | Glu | Arg | Pro | Thr | Tyr |
| | 210 | | | | | 215 | | | | | 220 | | | | |
| Thr | Asn | Leu | Asn | Arg | Leu | Val | Ser | Gln | Val | Ile | Ser | Ser | Leu | Ile | Ala |
| 225 | | | | | 230 | | | | | 235 | | | | | 240 |
| Ser | Leu | Arg | Phe | Asp | Gly | Ala | Leu | Lys | Val | Asp | Val | Asn | Glu | Phe | Gln |
| | | | | 245 | | | | | 250 | | | | | 255 | |
| Asp | Asn | Leu | Val | Pro | Tyr | Pro | Arg | Ile | His | Phe | Met | Leu | Ser | Ser | Tyr |
| | | | 260 | | | | | 265 | | | | | 270 | | |
| Ala | Pro | Val | Ile | Ser | Ala | Glu | Lys | Ala | Tyr | His | Glu | Gln | Leu | Ser | Val |
| | | 275 | | | | | 280 | | | | | 285 | | | |
| Ala | Glu | Ile | Thr | Asn | Ser | Ala | Phe | Glu | Pro | Ser | Ser | Met | Met | Ala | Lys |
| | 290 | | | | | 295 | | | | | 300 | | | | |
| Cys | Asp | Pro | Arg | His | Gly | Lys | Tyr | Met | Ala | Cys | Cys | Leu | Met | Tyr | Arg |
| 305 | | | | | 310 | | | | | 315 | | | | | 320 |
| Gly | Asp | Val | Val | Pro | Lys | Asp | Val | Asn | Ala | Ala | Val | Ala | Thr | Ile | Lys |
| | | | | 325 | | | | | 330 | | | | | 335 | |
| Thr | Lys | Arg | Thr | Ile | Gln | Phe | Val | Asp | Trp | Cys | Pro | Thr | Gly | Phe | Lys |
| | | | 340 | | | | | 345 | | | | | 350 | | |
| Cys | Gly | Ile | Asn | Tyr | Gln | Pro | Pro | Ser | Val | Val | Pro | Gly | Gly | Asp | Leu |
| | | 355 | | | | | 360 | | | | | 365 | | | |
| Ala | Lys | Val | Gln | Arg | Ala | Val | Cys | Met | Ile | Ser | Asn | Ser | Thr | Ser | Val |
| | 370 | | | | | 375 | | | | | 380 | | | | |
| Val | Glu | Val | Phe | Ser | Arg | Ile | Asp | His | Lys | Phe | Asp | Leu | Met | Tyr | Ala |
| 385 | | | | | 390 | | | | | 395 | | | | | 400 |
| Lys | Arg | Ala | Phe | Val | His | Trp | Tyr | Val | Gly | Glu | Gly | Met | Glu | Glu | Gly |
| | | | | 405 | | | | | 410 | | | | | 415 | |
| Glu | Phe | Ser | Glu | Ala | Arg | Glu | Asp | Leu | Ala | Ala | Leu | Glu | Lys | Asp | Tyr |
| | | | 420 | | | | | 425 | | | | | 430 | | |
| Glu | Glu | Val | Gly | Ala | Glu | Phe | Asp | Glu | Gly | Glu | Glu | Gly | Asp | Glu | Gly |
| | | 435 | | | | | 440 | | | | | 445 | | | |
| Asp | Glu | Tyr | | | | | | | | | | | | | |
| | 450 | | | | | | | | | | | | | | |